(12) United States Patent
Vaughan

(10) Patent No.: US 11,986,388 B2
(45) Date of Patent: May 21, 2024

(54) VALVE DELIVERY SYSTEM HAVING AN INTEGRAL DISPLACEMENT COMPONENT FOR MANAGING CHORDAE TENDINEAE IN SITU AND METHODS OF USE THEREOF

(71) Applicant: Medtronic Vascular, Inc., Santa Rosa, CA (US)

(72) Inventor: Brendan Vaughan, Clare (IE)

(73) Assignee: MEDTRONIC VASCULAR, INC., Santa Rosa, CA (US)

( * ) Notice: Subject to any disclaimer, the term of this patent is extended or adjusted under 35 U.S.C. 154(b) by 102 days.

(21) Appl. No.: 17/669,609

(22) Filed: Feb. 11, 2022

(65) Prior Publication Data

US 2022/0160498 A1 May 26, 2022

Related U.S. Application Data

(60) Continuation of application No. 16/451,377, filed on Jun. 25, 2019, now Pat. No. 11,273,034, which is a
(Continued)

(51) Int. Cl.
*A61F 2/24* (2006.01)

(52) U.S. Cl.
CPC ............ *A61F 2/243* (2013.01); *A61F 2/2433* (2013.01); *A61F 2/2436* (2013.01); *A61F 2/2418* (2013.01);
(Continued)

(58) Field of Classification Search
CPC ...... A61F 2/243; A61F 2/2436; A61F 2/2418; A61F 2210/0014
See application file for complete search history.

(56) References Cited

U.S. PATENT DOCUMENTS

| | | |
|---|---|---|
| 5,370,685 A | 12/1994 | Stevens |
| 5,916,193 A | 6/1999 | Stevens et al. |

(Continued)

FOREIGN PATENT DOCUMENTS

| | | |
|---|---|---|
| CN | 103860214 A | 6/2014 |
| EP | 1472996 A1 | 11/2004 |
| FR | 2945440 A1 | 11/2010 |

OTHER PUBLICATIONS

International Search Report and the Written Opinion of The International Searching Authority issued in PCT/US2017/057695, dated Jan. 31, 2018.
(Continued)

*Primary Examiner* — Alexander J Orkin
(74) *Attorney, Agent, or Firm* — MEDLER FERRO WOODHOUSE & MILLS PLLC

(57) ABSTRACT

Embodiments hereof relate methods of delivering a valve prosthesis to an annulus of a native valve of a heart. A valve delivery system is introduced into a ventricle of the heart via a ventricular wall of the heart. The valve delivery system has a displacement component at the distal portion thereof. The valve prosthesis is in a delivery configuration and the displacement component is in a delivery state in which the displacement component has a first outer diameter. While the valve prosthesis is in the delivery configuration, the displacement component of the valve delivery system is radially expanded into an expanded state in which the displacement component has a second outer diameter greater than the first outer diameter. The valve delivery system is advanced towards the annulus of the native valve of the heart with the displacement component in the expanded state to displace chordae tendineae.

19 Claims, 29 Drawing Sheets

Related U.S. Application Data division of application No. 15/346,955, filed on Nov. 9, 2016, now Pat. No. 10,368,988.

(52) U.S. Cl.
CPC ................ *A61F 2210/0014* (2013.01); *A61F 2250/0003* (2013.01)

(56) References Cited

U.S. PATENT DOCUMENTS

| | | | |
|---|---|---|---|
| 5,957,949 | A | 9/1999 | Leonhardt et al. |
| 6,277,136 | B1 | 8/2001 | Bonutti |
| 7,621,948 | B2 | 11/2009 | Hermann et al. |
| 8,105,375 | B2 | 1/2012 | Navia et al. |
| 8,591,460 | B2 | 11/2013 | Wilson et al. |
| 9,034,032 | B2 | 5/2015 | Mclean et al. |
| 9,078,994 | B2 | 7/2015 | Rosenman et al. |
| 11,273,034 | B2 * | 3/2022 | Anderson ................ A61F 2/243 |
| 2004/0260394 | A1 | 12/2004 | Donk et al. |
| 2006/0265056 | A1 | 11/2006 | Nguyen et al. |
| 2007/0083082 | A1 | 4/2007 | Kiser et al. |
| 2007/0239266 | A1 | 10/2007 | Birdsall |
| 2007/0239269 | A1 | 10/2007 | Dolan et al. |
| 2008/0071361 | A1 | 3/2008 | Tuval et al. |
| 2008/0306442 | A1 | 12/2008 | Bardsley et al. |
| 2010/0191326 | A1* | 7/2010 | Alkhatib ................ A61F 2/2439 623/2.11 |
| 2011/0208297 | A1 | 8/2011 | Tuval et al. |
| 2012/0035722 | A1 | 2/2012 | Tuval |
| 2012/0059458 | A1 | 3/2012 | Buchbinder et al. |
| 2012/0078237 | A1 | 3/2012 | Wang et al. |
| 2012/0101572 | A1 | 4/2012 | Kovalsky et al. |
| 2012/0271411 | A1 | 10/2012 | Duhay et al. |
| 2013/0060328 | A1 | 3/2013 | Rothstein |
| 2013/0079872 | A1 | 3/2013 | Gallagher |
| 2013/0190861 | A1 | 7/2013 | Chau et al. |
| 2013/0226290 | A1 | 8/2013 | Yellin et al. |
| 2013/0231735 | A1 | 9/2013 | Deem et al. |
| 2013/0253571 | A1 | 9/2013 | Bates |
| 2013/0310928 | A1 | 11/2013 | Morriss et al. |
| 2014/0039611 | A1 | 2/2014 | Lane et al. |
| 2014/0067049 | A1 | 3/2014 | Costello |
| 2014/0148889 | A1 | 5/2014 | Deshmukh et al. |
| 2014/0277404 | A1 | 9/2014 | Wilson et al. |
| 2014/0277405 | A1 | 9/2014 | Wilson et al. |
| 2014/0350660 | A1 | 11/2014 | Cocks et al. |
| 2014/0350669 | A1 | 11/2014 | Gillespie et al. |
| 2014/0371843 | A1 | 12/2014 | Wilson et al. |
| 2014/0379074 | A1 | 12/2014 | Spence et al. |
| 2015/0119981 | A1 | 4/2015 | Khairkhahan et al. |
| 2015/0142100 | A1* | 5/2015 | Morriss ................ A61F 2/2409 623/2.4 |
| 2015/0238315 | A1 | 8/2015 | Rabito et al. |
| 2015/0289975 | A1 | 10/2015 | Costello |
| 2015/0297346 | A1 | 10/2015 | Duffy et al. |
| 2015/0305869 | A1 | 10/2015 | Styrc |
| 2016/0045350 | A1 | 2/2016 | Berra |
| 2016/0175565 | A1 | 6/2016 | Schaffer |
| 2016/0213470 | A1 | 7/2016 | Ahlberg et al. |
| 2016/0235531 | A1 | 8/2016 | Ciobanu et al. |
| 2017/0056169 | A1 | 3/2017 | Johnson et al. |
| 2018/0049873 | A1 | 2/2018 | Manash |

OTHER PUBLICATIONS

Notification Concerning Transmittal of Copy of International Preliminary Report on Patentability issued in International Application No. PCT/US2017/057683 dated May 23, 2019.

Office Action dated Sep. 2, 2021 in Chinese Patent Appl No. 201780069092.0 (with English-language translation).

* cited by examiner

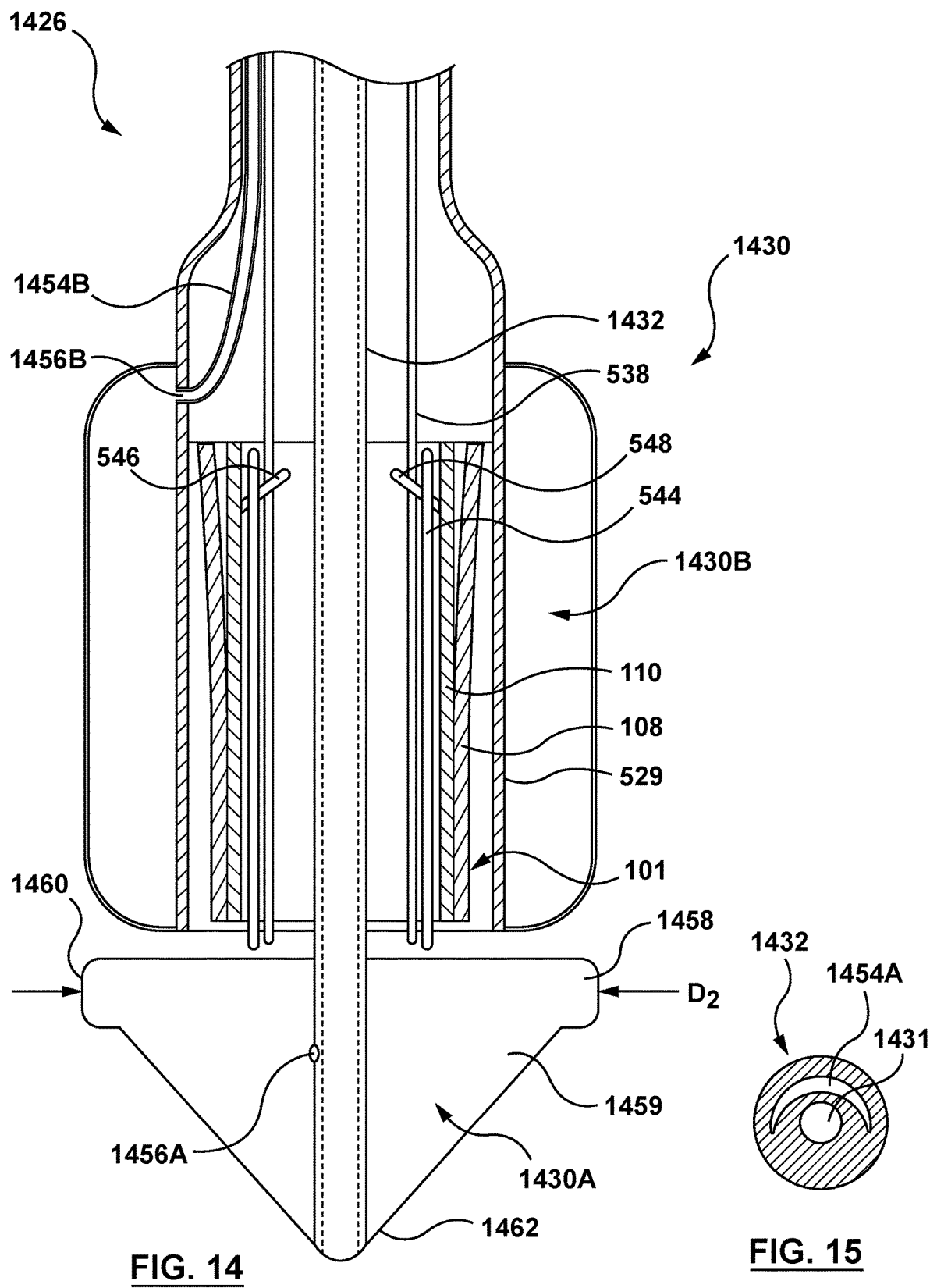

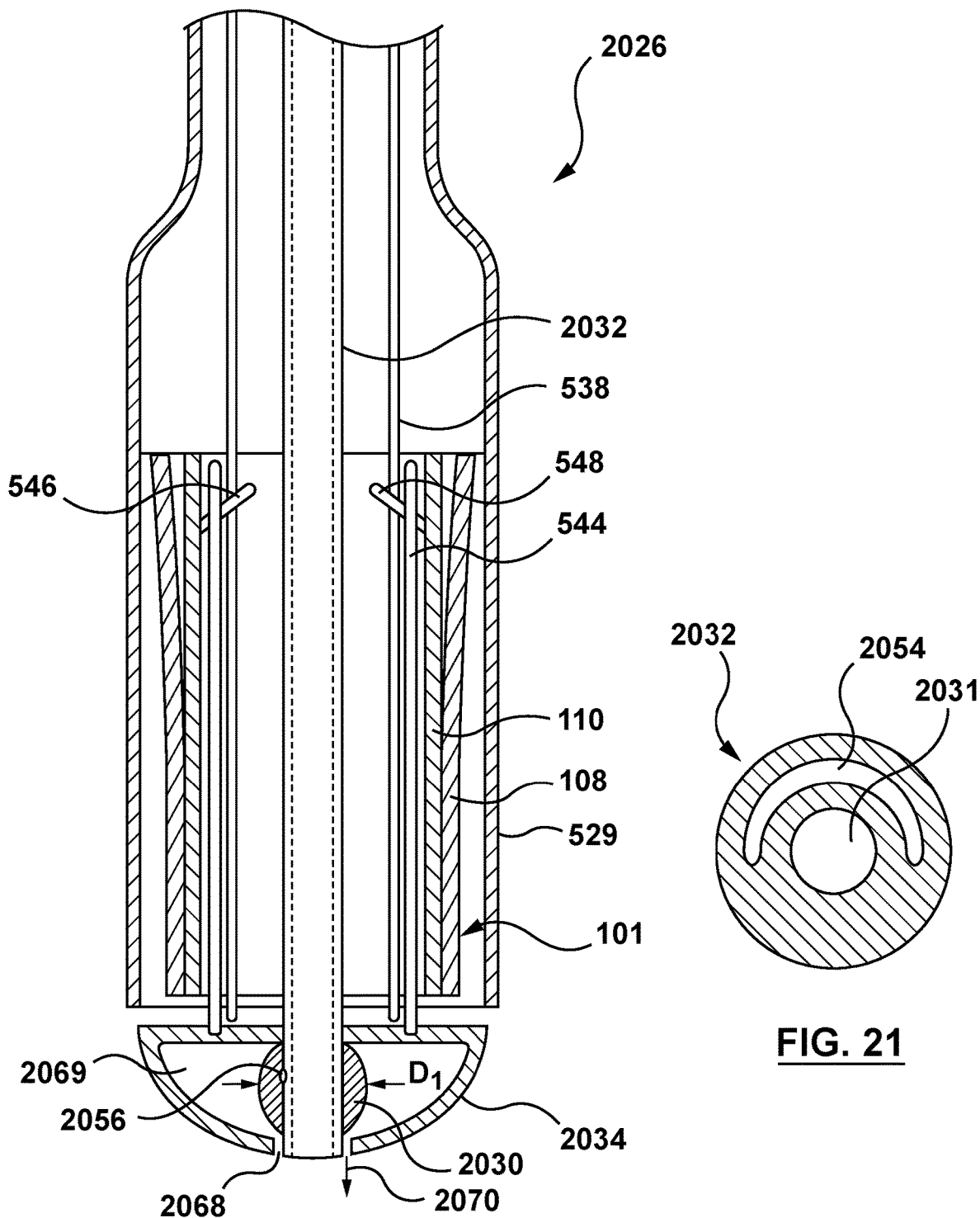

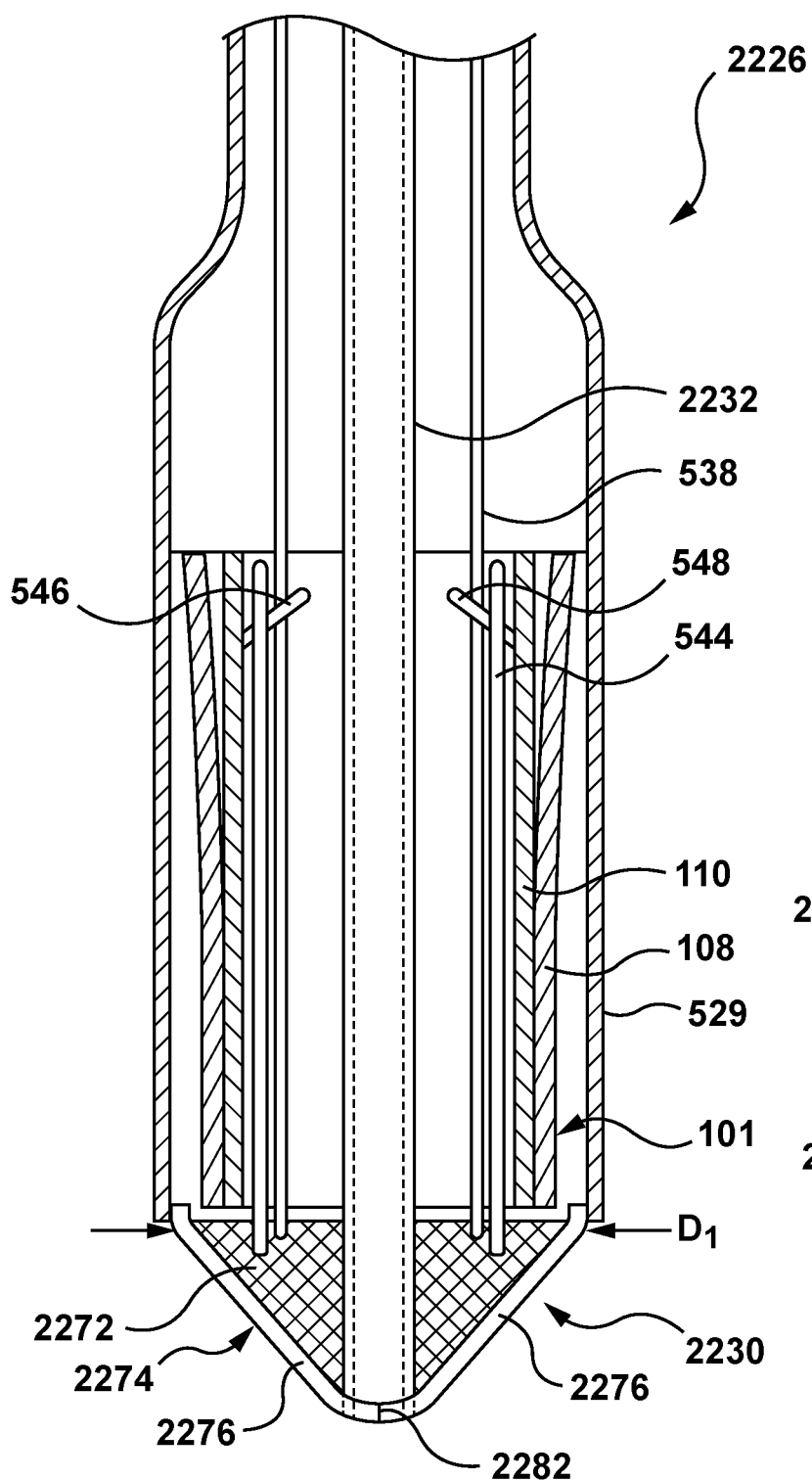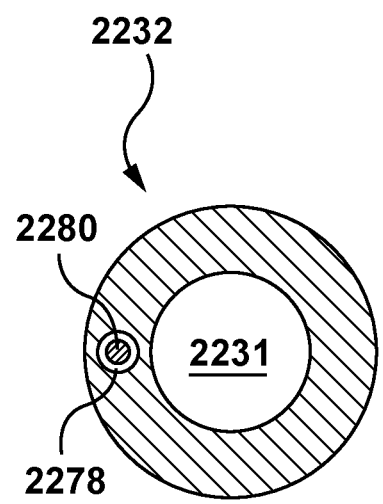
FIG. 22
FIG. 23

VALVE DELIVERY SYSTEM HAVING AN INTEGRAL DISPLACEMENT COMPONENT FOR MANAGING CHORDAE TENDINEAE IN SITU AND METHODS OF USE THEREOF

CROSS-REFERENCE TO RELATED APPLICATION

This application is a continuation of U.S. application Ser. No. 16/451,377, filed Jun. 25, 2019, which is a divisional of U.S. application Ser. No. 15/346,955, filed Nov. 9, 2016, now U.S. Pat. No. 10,368,988, each of which is incorporated by reference herein in its entirety.

FIELD OF THE INVENTION

The invention relates to valve prostheses and more particularly to valve delivery systems configured to manage chordae tendineae during delivery of valve prostheses in situ.

BACKGROUND OF THE INVENTION

A wide range of medical treatments are known that utilize "endoluminal prostheses." As used herein, endoluminal prostheses are intended to include medical devices that are adapted for temporary or permanent implantation within a body lumen, including both naturally occurring and artificially made lumens. Examples of lumens in which endoluminal prostheses may be implanted include but are not limited to arteries, veins, gastrointestinal tract, biliary tract, urethra, trachea, hepatic and cerebral shunts, and fallopian tubes.

Stent prostheses are known for implantation within a body lumen for providing artificial radial support to the wall tissue that defines the body lumen. To provide radial support to a blood vessel, such as one that has been widened by a percutaneous transluminal coronary angioplasty, commonly referred to as "angioplasty," "PTA" or "PTCA", a stent may be implanted in conjunction with the procedure. Under this procedure, the stent may be collapsed to an insertion diameter and inserted into the vasculature at a site remote from the diseased vessel. The stent may then be delivered to the desired treatment site within the affected vessel and deployed, by self-expansion or radial expansion, to its desired diameter for treatment.

Recently, flexible prosthetic valves supported by stent structures that can be delivered percutaneously using a catheter-based delivery system have been developed for heart and venous valve replacement. These prosthetic valves may include either self-expanding or balloon-expandable stent structures with valve leaflets disposed within the interior of the stent structure. The prosthetic valve can be reduced in diameter, by being contained within a sheath component of a valve delivery system or by crimping onto a balloon catheter, and advanced through the venous or arterial vasculature. Once the prosthetic valve is positioned at the treatment site, for instance within an incompetent native or previously implanted prosthetic valve, the stent structure may be expanded to hold the prosthetic valve firmly in place. One embodiment of a prosthetic valve having a stent structure is disclosed in U.S. Pat. No. 5,957,949 to Leonhardt et al. entitled "Percutaneous Placement Valve Stent," which is incorporated by reference herein in its entirety.

A human heart includes two atrio-ventricular valves through which blood flows from the atria to the ventricles, the valves functioning to prevent return of blood to the atrium. The tricuspid valve, also known as the right atrioventricular valve, is a tri-flap valve located between the right atrium and the right ventricle. The mitral valve, also known as the bicuspid or left atrioventricular valve, is a dual-flap valve located between the left atrium and the left ventricle, and serves to direct oxygenated blood from the lungs through the left side of the heart and into the aorta for distribution to the body. As with other valves of the heart, the mitral valve is a passive structure in that it does not itself expend any energy and does not perform any active contractile function. The mitral valve includes two moveable leaflets, an anterior leaflet and a posterior leaflet, that each open and close in response to differential pressures on either side of the valve. Ideally, the leaflets move apart from each other when the valve is in an open position, and meet or "coapt" when the valve is in a closed position. Problems that may develop with valves include stenosis in which a valve does not open properly, and/or insufficiency or regurgitation in which a valve does not close properly. Stenosis and insufficiency may occur concomitantly in the same valve. The effects of valvular dysfunction vary, with mitral regurgitation or backflow typically having relatively severe physiological consequences to the patient.

Chordae tendineae extend within the left ventricle between the native leaflets of the mitral valve and the papillary muscles. Chordae tendineae are cord-like tendons that connect the medial papillary muscle to the posterior leaflet of the mitral valve and connect the lateral papillary muscle to the anterior leaflet of the mitral valve. One method of delivering a mitral valve prosthesis includes delivery via a transapical approach directly through the apex of the heart via a thoracotomy. However, during such a transapical approach, the chordae tendineae may act as an obstacle within the delivery pathway. Chordae tendineae are not all aligned the same way making the delivery pathway to the mitral valve more challenging. The valve delivery system may become entangled in chordae tendineae during advancement, thereby restricting movement of the valve delivery system within the anatomy and also preventing accurate alignment and/or deployment of the valve prosthesis.

Due to the different physical characteristics of the mitral valve as compared to other valves, implantation of a valve in the mitral position has its own unique requirements for valve replacement. There is a continued desire to improve mitral valve replacement devices and procedures to accommodate the structure of the heart, including by providing improved devices and methods for replacing the mitral valve percutaneously. Embodiments hereof relate to methods and devices for managing chordae tendineae during a transapical valve replacement procedure.

BRIEF SUMMARY OF THE INVENTION

Embodiments hereof relate to methods of delivering a valve prosthesis to an annulus of a native valve of a heart, the native valve having chordae tendineae. A valve delivery system is introduced into a ventricle of the heart via a ventricular wall of the heart. The valve delivery system has the valve prosthesis at a distal portion thereof and a displacement component at the distal portion thereof, the displacement component being configured to be radially expandable between a first outer diameter and a second outer diameter. The valve prosthesis is in a delivery configuration and the displacement component is in a delivery state in which the displacement component has the first outer diameter. While the valve prosthesis is in the delivery configuration, the displacement component of the valve delivery system is radially expanded into an expanded state in which the displacement component has the second outer diameter greater than the first outer diameter. The valve delivery system is advanced towards the annulus of the native valve of the heart with the displacement component in the expanded state, wherein the second outer diameter is of a dimension that prevents the displacement component from passing through openings between chordae in the ventricle so that the displacement component in the expanded state pushes chordae in the ventricle radially outward away from the valve delivery system. The valve prosthesis is deployed into apposition with the annulus of the native valve.

BRIEF DESCRIPTION OF DRAWINGS

The foregoing and other features and advantages of the invention will be apparent from the following description of embodiments hereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

FIG. 14 is an enlarged sectional view of a distal portion of a valve delivery system according to another embodiment hereof, wherein the valve delivery system includes a displacement component which includes two balloons and the displacement component is in an expanded or inflated state.

FIG. 15 is a cross-sectional view of an inner shaft of the valve delivery system of FIG. 14, wherein the inner shaft is shown removed from the valve delivery system for illustrative purposes only.

FIG. 20 is an enlarged sectional view of a distal portion of a valve delivery system according to another embodiment hereof, wherein the valve delivery system includes a displacement component which is housed within a hollow distal tip and mounted on a slidable inner shaft and the displacement component is in an unexpanded or uninflated state.

FIG. 21 is a cross-sectional view of an inner shaft of the valve delivery system of FIG. 20, wherein the inner shaft is shown removed from the valve delivery system for illustrative purposes only.

FIG. 22 is an enlarged sectional view of a distal portion of a valve delivery system according to another embodiment hereof, wherein the valve delivery system includes a displacement component including a plurality of spokes and a planar element and the displacement component is in an unexpanded or delivery state.

FIG. 23 is a cross-sectional view of an inner shaft of the valve delivery system of FIG. 22, wherein the inner shaft is shown removed from the valve delivery system for illustrative purposes only.

DETAILED DESCRIPTION OF THE INVENTION

Specific embodiments of the present invention are now described with reference to the figures, wherein like reference numbers indicate identical or functionally similar elements. Unless otherwise indicated, the terms "distal" and "proximal" are used in the following description with respect to a position or direction relative to the treating clinician. "Distal" and "distally" are positions distant from or in a direction away from the clinician, and "proximal" and "proximally" are positions near or in a direction toward the clinician. In addition, the term "self-expanding" is used in the following description and is intended to convey that the structures are shaped or formed from a material that can be provided with a mechanical memory to return the structure from a compressed or constricted delivery configuration to an expanded deployed configuration. Non-exhaustive exemplary self-expanding materials include stainless steel, a pseudo-elastic metal such as a nickel titanium alloy or nitinol, various polymers, or a so-called super alloy, which may have a base metal of nickel, cobalt, chromium, or other metal. Mechanical memory may be imparted to a wire or scaffold structure by thermal treatment to achieve a spring temper in stainless steel, for example, or to set a shape memory in a susceptible metal alloy, such as nitinol. Various polymers that can be made to have shape memory characteristics may also be suitable for use in embodiments hereof to include polymers such as polynorborene, trans-polyisoprene, styrene-butadiene, and polyurethane. As well poly L-D lactic copolymer, oligo caprylactone copolymer and polycyclooctene can be used separately or in conjunction with other shape memory polymers.

The following detailed description is merely exemplary in nature and is not intended to limit the invention or the application and uses of the invention. Although the description of embodiments hereof are in the context of delivery systems for delivering a valve prosthesis within a native mitral valve, the valve delivery systems described herein can also be used in other valves of the body that include chordae tendineae, such as for delivering a valve prosthesis within a native tricuspid valve, or for delivering a mitral or tricuspid valve prosthesis within a failed previously-implanted prosthesis. Furthermore, there is no intention to be bound by any expressed or implied theory presented in the preceding technical field, background, brief summary or the following detailed description.

Figure 1:
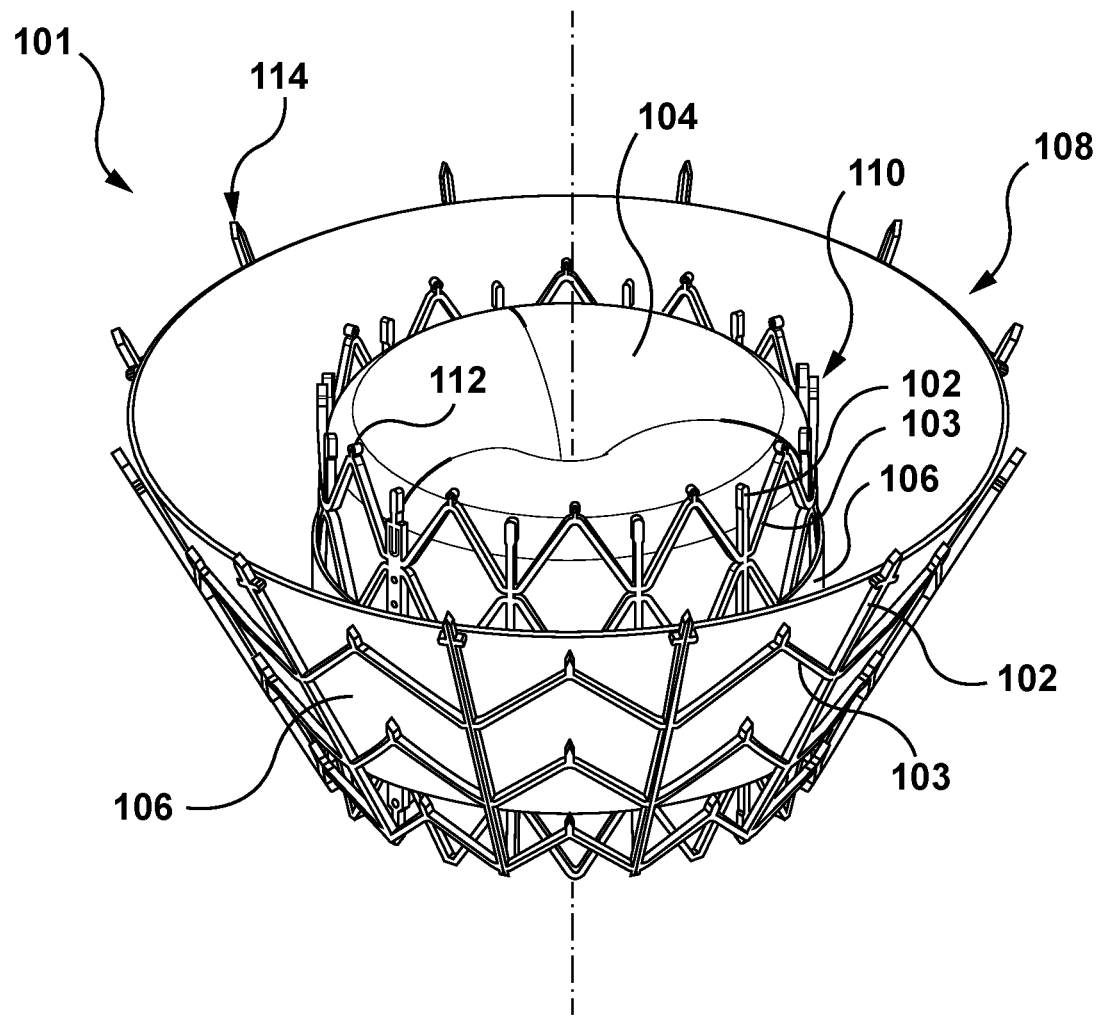
FIG. 1 is a perspective view of an exemplary transcatheter heart valve prosthesis for use in embodiments hereof, the heart valve prosthesis in its expanded or deployed configuration.

Embodiments hereof are related to a valve prosthesis configured for deployment within a native heart valve of the heart in a transcatheter heart valve implantation procedure. FIG. 1 is a perspective view of an exemplary transcatheter valve prosthesis 101 for use in embodiments hereof, wherein the valve prosthesis is in an expanded, deployed configuration in accordance with an embodiment hereof. Valve prosthesis 101 is illustrated herein in order to facilitate description of the chordae management methods and devices to be utilized in conjunction with a valve delivery system according to embodiments hereof. It is understood that any number of alternate heart valve prostheses can be used with the methods and devices described herein. Valve prosthesis 101 is merely exemplary and is similar to heart valve prostheses described in more detail in U.S. Pat. No. 9,034,032 to McLean et al., which is herein incorporated by reference in its entirety. Other non-limiting examples of transcatheter valve prostheses useful with systems and methods of the present disclosure are described in U.S. Patent Application Publication Nos. 2012/0101572 to Kovalsky et al., 2012/0035722 to Tuval U.S. Pat. Appl. Pub. No. 2006/0265056 to Nguyen et al., U.S. Pat. Appl. Pub. No. 2007/05409266 to Birdsall, U.S. Pat. Appl. Pub. No. 2007/05409269 to Dolan et al., and U.S. Pat. Appl. Pub. No. 2008/00713548 to Tuval, each of which is incorporated by reference herein in its entirety and illustrate heart valve prostheses configured for placement in a mitral valve.

As shown in FIG. 1, heart valve prosthesis 101 includes a flexible anchoring member 108 at least partially surrounding and coupled to an inner valve support 110. Heart valve prosthesis 101 further includes a prosthetic valve component 104 coupled to, mounted within, or otherwise carried by valve support 110. Heart valve prosthesis 101 also includes one or more sealing members 106 and tissue engaging elements 114. For example, tissue engaging elements 114 may be spikes disposed on an upstream perimeter of anchoring member 108 and extend in an upward and/or radially outward direction to engage, and in some embodiments, penetrate the native tissue to facilitate retention or maintain position of the device in a desired implanted location. In another specific embodiment, sealing member 140 may extend around an inner wall of anchoring member 108 and/or around an exterior surface of valve support 110 to prevent paravalvular leaks between heart valve prosthesis 101 and the native tissue and/or between anchoring member 108 and valve support 110. Tissue engaging elements 114 may also be included around an outer wall of anchoring member 108 and may extend outwardly to engage and, in some embodiments, penetrate the native valve leaflets or other adjacent tissue. Additionally, valve support 110 may have a plurality of coupling features 112, such as eyelets, around an upstream end to facilitate loading, retention and deployment of heart valve prosthesis 101 within and from a delivery catheter (not shown), as further described herein.

Valve support 110 is a generally cylindrical stent or frame that supports a prosthetic valve component 104 within the interior thereof. Similarly, anchoring member 108 is also a stent or frame having a flared, funnel-like or hyperboloid shape. In some embodiments, valve support 110 and/or anchoring member 108 includes a plurality of posts 102 connected circumferentially by a plurality of struts 103. Posts 102 and struts 103 may be arranged in a variety of geometrical patterns that may expand and provide sufficient resilience and column strength for maintaining the integrity of prosthetic valve component 104. For example, posts 102 may extend longitudinally across multiple rows of struts 103 to provide column strength to the valve support 110. Generally, the plurality of posts 102 may extend along an axial direction generally parallel to the longitudinal axis and the struts 103 may extend circumferentially around and transverse to the longitudinal axis. As will be understood by one of ordinary skill in the art, the stent or frame of a valve prosthesis may have other configurations such as a metallic, polymeric, or fabric mesh or a woven construction. In embodiments hereof, valve support 110 is self-expanding to return to an expanded deployed state from a compressed or constricted delivery state and may be made from stainless steel, a pseudo-elastic metal such as a nickel titanium alloy or Nitinol, or a so-called super alloy, which may have a base metal of nickel, cobalt, chromium, or other metal. "Self-expanding" as used herein means that a structure/component has a mechanical memory to return to the expanded or deployed configuration as described herein. Alternatively, valve prosthesis 101 may be balloon-expandable as would be understood by one of ordinary skill in the art. Whether valve support 110 is self-expanding or balloon-expandable, valve prosthesis 101 has a compressed configuration for delivery within a valve delivery system and a radially expanded configuration for deployment within an annulus of the native valve site. In some embodiments, anchoring member 108 and/or valve support 110 may be laser cut from a single metal tube into the desired geometry, creating a tubular scaffold of interconnected struts. Anchoring member 108 may then be shaped into a desired configuration, e.g. a flared, funnel-like or hyperboloid shape, using known shape-setting techniques for such materials.

As previously mentioned, valve prosthesis 101 includes prosthetic valve component 104 within the interior of valve support 110. Prosthetic valve component 104 is configured as a one-way valve to allow blood flow in one direction and thereby regulate blood flow there-through. Prosthetic valve component 104 is capable of blocking flow in one direction to regulate flow there-through via valve leaflets that may form a bicuspid or tricuspid replacement valve. More particularly, if valve prosthesis 101 is configured for placement within a native valve having two leaflets such as the mitral valve, prosthetic valve component 104 includes two valve leaflets to form a bicuspid replacement valve that closes with pressure on the outflow and opens with pressure on the inflow. In other embodiments in accordance herewith, the prosthetic valve component may be a tricuspid replacement valve or may be a single leaflet replacement valve. The valve leaflets are sutured or otherwise securely and sealingly attached to an inner circumference of valve support 110 and/or sealing members 106 which encloses or lines valve support 110 as would be known to one of ordinary skill in the art of prosthetic tissue valve construction.

The valve leaflets may be made of pericardial material; however, the leaflets may instead be made of another material. Natural tissue for prosthetic valve leaflets for use in prosthetic valve component 104 may be obtained from, for example, heart valves, aortic roots, aortic walls, aortic leaflets, pericardial tissue, such as pericardial patches, bypass grafts, blood vessels, intestinal submucosal tissue, umbilical tissue and the like from humans or animals, such as tissue from bovine, equine or porcine origins. Synthetic materials suitable for use as prosthetic valve leaflets in embodiments hereof include DACRON® polyester commercially available from Invista North America S.A.R.L. of Wilmington, DE, polyurethane, Gore-Tex or other cloth materials, nylon blends, polymeric materials, and vacuum deposition nitinol fabricated materials. One polymeric material from which the replacement valve leaflets may be made is an ultra-high molecular weight polyethylene material commercially available under the trade designation DYNEEMA from Royal DSM of the Netherlands. With certain prosthetic leaflet materials, it may be desirable to coat one or both sides of the replacement valve leaflet with a material that will prevent or minimize overgrowth. It is further desirable that the prosthetic leaflet material is durable and not subject to stretching, deforming, or fatigue.

Sealing members 106 are formed from a suitable graft material such as a natural or biological material such as pericardium or another membranous tissue such as intestinal submucosa. Alternatively, sealing members 106 may be a low-porosity woven fabric, such as polyester, Dacron fabric, or PTFE, which creates a one-way fluid passage when attached to the stent. In one embodiment, sealing members 106 may be a knit or woven polyester, such as a polyester or PTFE knit, which can be utilized when it is desired to provide a medium for tissue ingrowth and the ability for the fabric to stretch to conform to a curved surface. Polyester velour fabrics may alternatively be used, such as when it is desired to provide a medium for tissue ingrowth on one side and a smooth surface on the other side. These and other appropriate cardiovascular fabrics are commercially available from Bard Peripheral Vascular, Inc. of Tempe, Ariz., for example.

Figure 2:
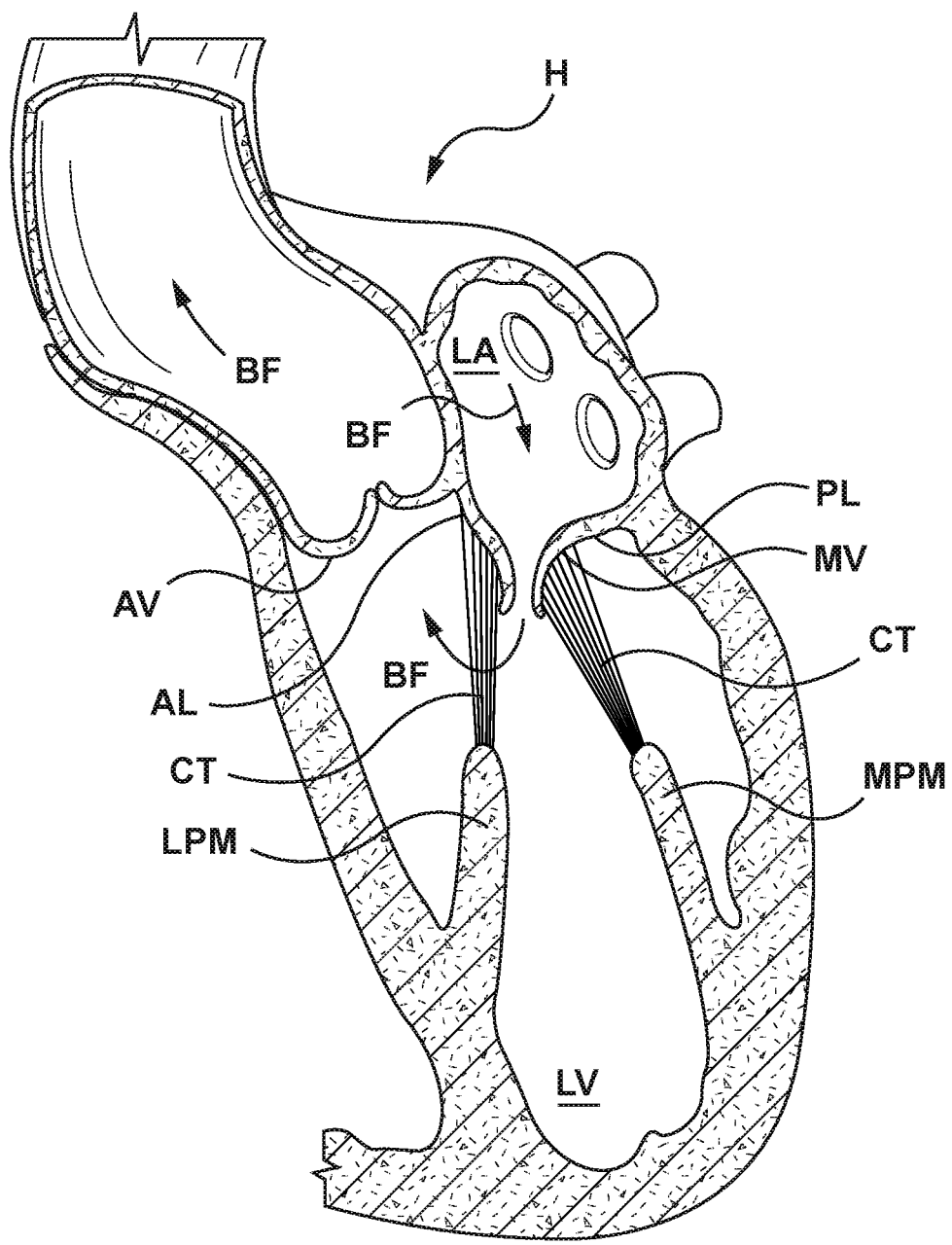
FIG. 2 is a sectional view illustration of the anatomy of a native mitral valve.

FIG. 2 illustrates a sectional view of a heart H, illustrating a left atrium LA, a left ventricle LV, a mitral valve MV and an aortic valve AV. Blood flow BF is depicted with directional arrows in FIG. 2 in the left atrium LA, into left ventricle LV through mitral valve MV, and into the aorta through aortic valve AV. Mitral valve MV is saddle-shaped and includes two native leaflets, posterior leaflet PL and anterior leaflet AL, and chordae tendineae CT extend within the left ventricle LV between the native leaflets of the mitral valve MV and the papillary muscles. As previously described herein, chordae tendineae CT are cord-like tendons that connect the medial papillary muscle MPM to the posterior leaflet PL of the mitral valve MV and connect the lateral papillary muscle LPM to the anterior leaflet AL of the mitral valve MV. When the native mitral valve is operating properly, the native leaflets will generally function in such a way that blood flows toward the left ventricle LV when the leaflets are in an open position, and so that blood is prevented from moving toward the left atrium LA when the leaflets are in a closed position. During systole, when the native leaflets close to prevent backflow of blood into the atrium, the chordae tendineae CT assist in preventing the native leaflets from everting or prolapsing into the atrium by becoming tense and holding the native leaflets in the closed position.

Figure 3:
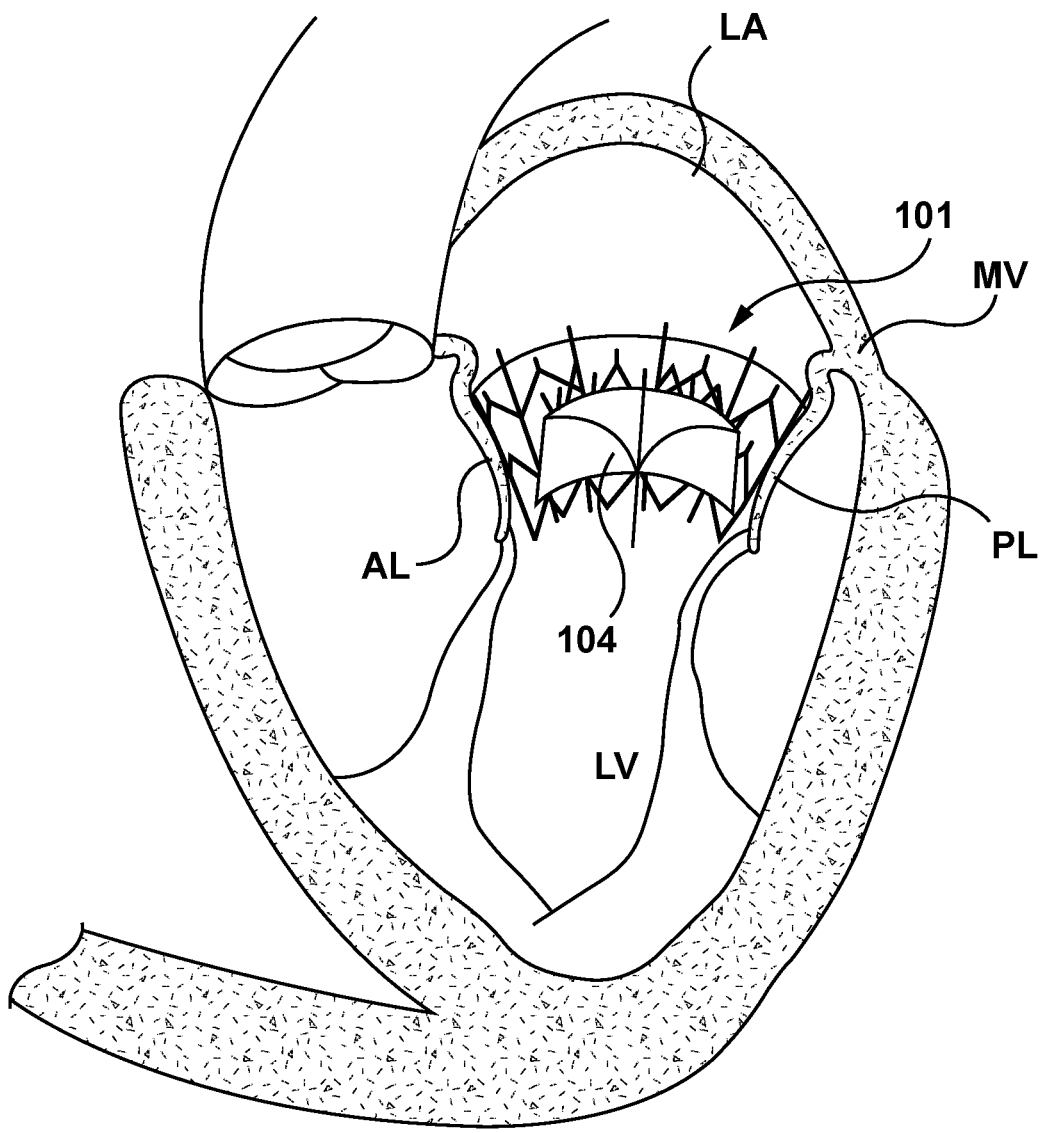
FIG. 3 is a sectional view illustration of the heart valve prosthesis of FIG. 1 implanted within a native mitral valve annulus.

FIG. 3 is an illustration of valve prosthesis 101 implanted within a native mitral heart valve, which is shown in section. Valve prosthesis 101 is shown deployed within a native mitral valve, with an upstream end thereof extending into the left ventricle and a downstream end thereof extending into the left atrium. When valve prosthesis 101 is deployed within the valve annulus of a native heart valve, valve support 110 and anchoring member 108 expands within native valve leaflets, posterior leaflet PL and anterior leaflet AL, of the patient's defective valve, retaining the native valve leaflets in a permanently open state.

Figure 4:
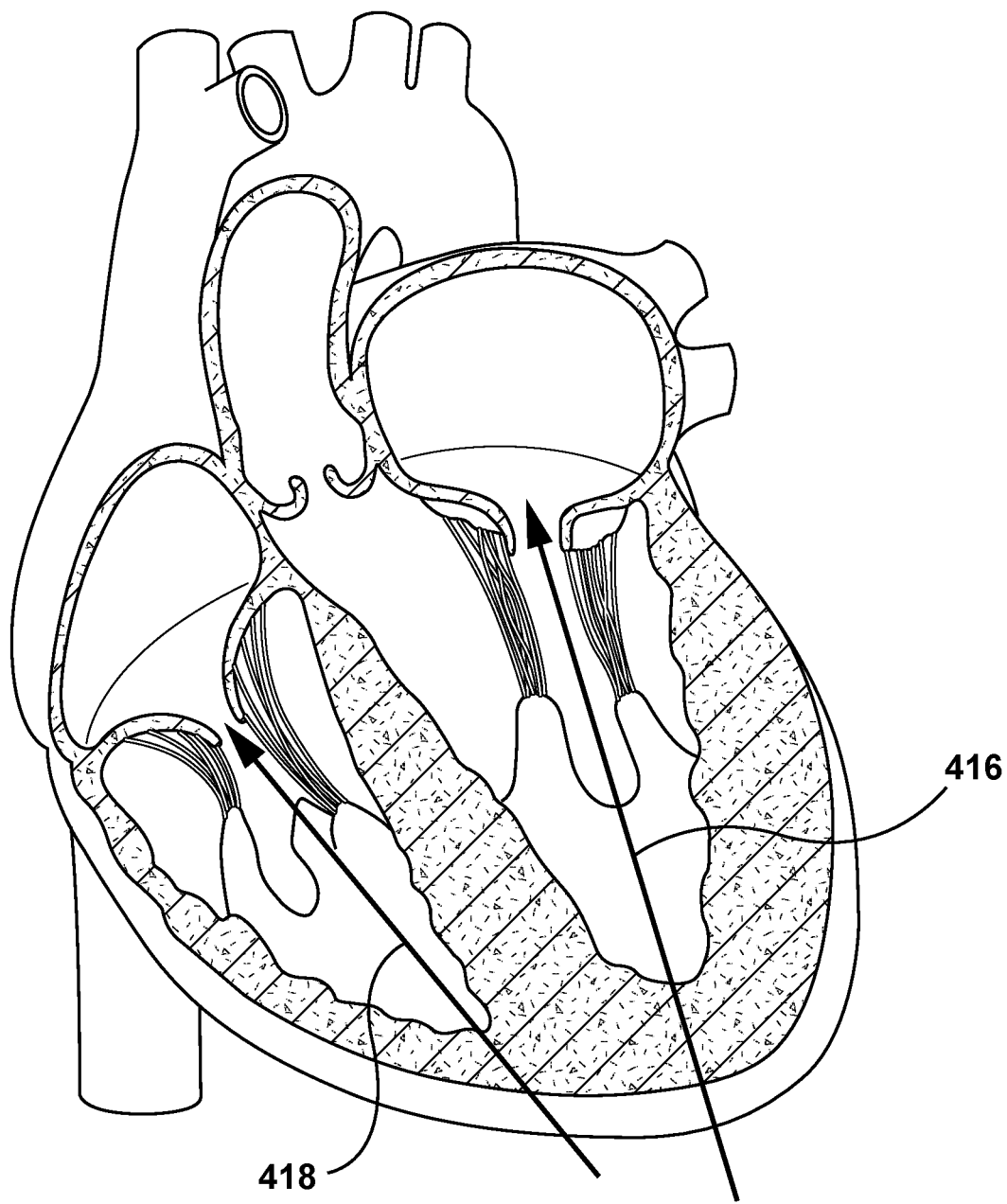
FIG. 4 is a sectional view illustration of the anatomy of heart illustrating exemplary transapical delivery pathways or routes for a transcatheter valve prosthesis.

One method of delivering valve prosthesis 101 includes delivery via a transapical approach directly through the apex of the heart via a thoracotomy, as best illustrated in FIG. 4. FIG. 4 is a sectional view illustration of the anatomy of heart illustrating an exemplary transapical delivery pathway or route represented by directional arrow 416 for delivery of valve prosthesis 101 to the native mitral valve, located between the left atrium and left ventricle. FIG. 4 also illustrates an exemplary transapical delivery pathway or route represented by directional arrow 418 for delivery of a valve prosthesis to the native tricuspid valve, located between the right atrium and right ventricle. In a transapical approach, access to the heart is gained via thoracic incision, which can be a conventional open thoracotomy or sternotomy, or a smaller intercostal or sub-xyphoid incision or puncture. An access cannula is then placed through a puncture, sealed by a purse-string suture, in the wall of the left ventricle at or near the apex of the heart. Valve delivery systems described herein may then be introduced into the left ventricle through this access cannula. The transapical approach has the feature of providing a shorter, straighter, and more direct path to the mitral or tricuspid valve. Further, because it does not involve intravascular access, the transapical procedure can be performed by surgeons who may not have the necessary training in interventional cardiology to perform the catheterizations required in other percutaneous approaches. During delivery, if self-expanding, the valve prosthesis remains compressed until it reaches a target diseased native heart valve, at which time the valve prosthesis can be released from the valve delivery system and expanded in situ via self-expansion. The valve delivery system is then removed and valve prosthesis 101 remains deployed within the native target heart valve. Alternatively, valve prosthesis 101 may be balloon-expandable and delivery thereof may be accomplished via a balloon catheter as would be understood by one of ordinary skill in the art.

However, as previously described herein, the chordae tendineae may act as an obstacle within delivery pathways 416, 418 when valve prosthesis 101 is delivered transapically and the valve delivery system may become entangled in chordae tendineae during advancement. Embodiments hereof relate to methods and devices for managing chordae tendineae during a transapical valve replacement procedure. More particularly, embodiments hereof relate to a valve delivery system 520 having a displacement component 530 integrated into or onto the valve delivery system to displace chordae tendineae and thereby clear a pathway for the valve delivery system. Displacement component 530 is configured to be radially expandable between a first outer diameter and a second outer diameter in order to relocate or displace the chordae tendineae which interfere with mitral or tricuspid access from the apex. The first outer diameter is not greater than an outer diameter of the outer shaft and the second outer diameter is greater than the outer diameter of the outer shaft. The second outer diameter is of a dimension that prevents displacement component 530 from passing through openings between chordae in a left ventricle so that displacement component 530 in the expanded state displaces or pushes chordae in a ventricle radially outward away from the valve delivery system.

Figures 5, 5A:
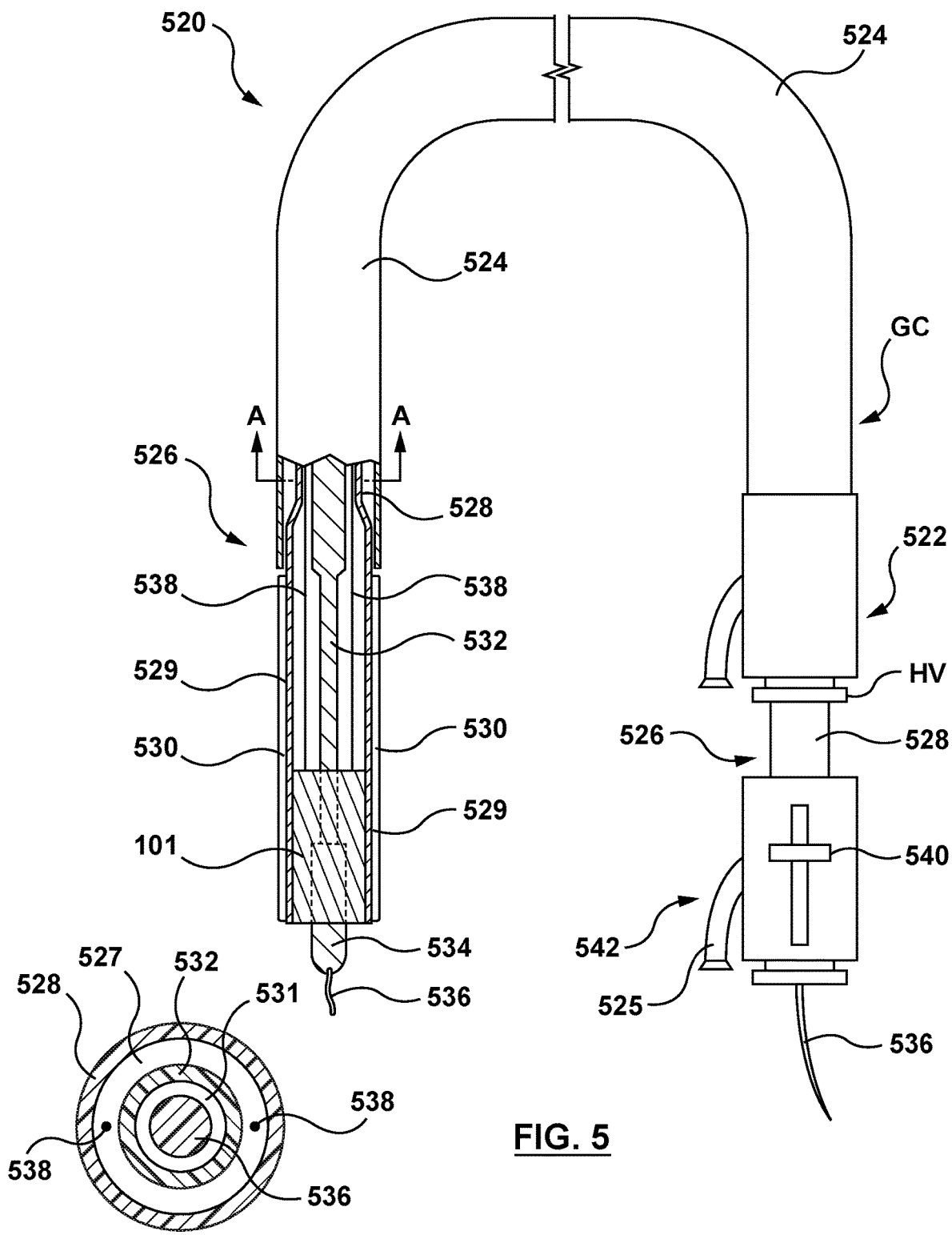
FIG. 5 is an illustration of a valve delivery system having a displacement component at a distal end thereof according to an embodiment hereof, wherein the displacement component is in a delivery or unexpanded state.
FIG. 5A is a cross-sectional view taken along line A-A of FIG. 5.

FIG. 5 is a side view of valve delivery system 520 according to an embodiment thereof which may be used to deliver and deploy heart valve prosthesis 101 disclosed herein to the heart of a patient. Valve delivery system 520 includes a guiding catheter GC and a valve delivery catheter 526. Guiding catheter GC has a handle 522 coupled to a delivery shaft 524, which in one embodiment is 34 F or less, and in another embodiment, 28 F or less in diameter. Guiding catheter GC may be steerable or preshaped in a configuration suitable for the particular approach to the target valve. Valve delivery catheter 526 is placed through a hemostasis valve HV on a proximal end of guiding catheter GC.

Figure 6:
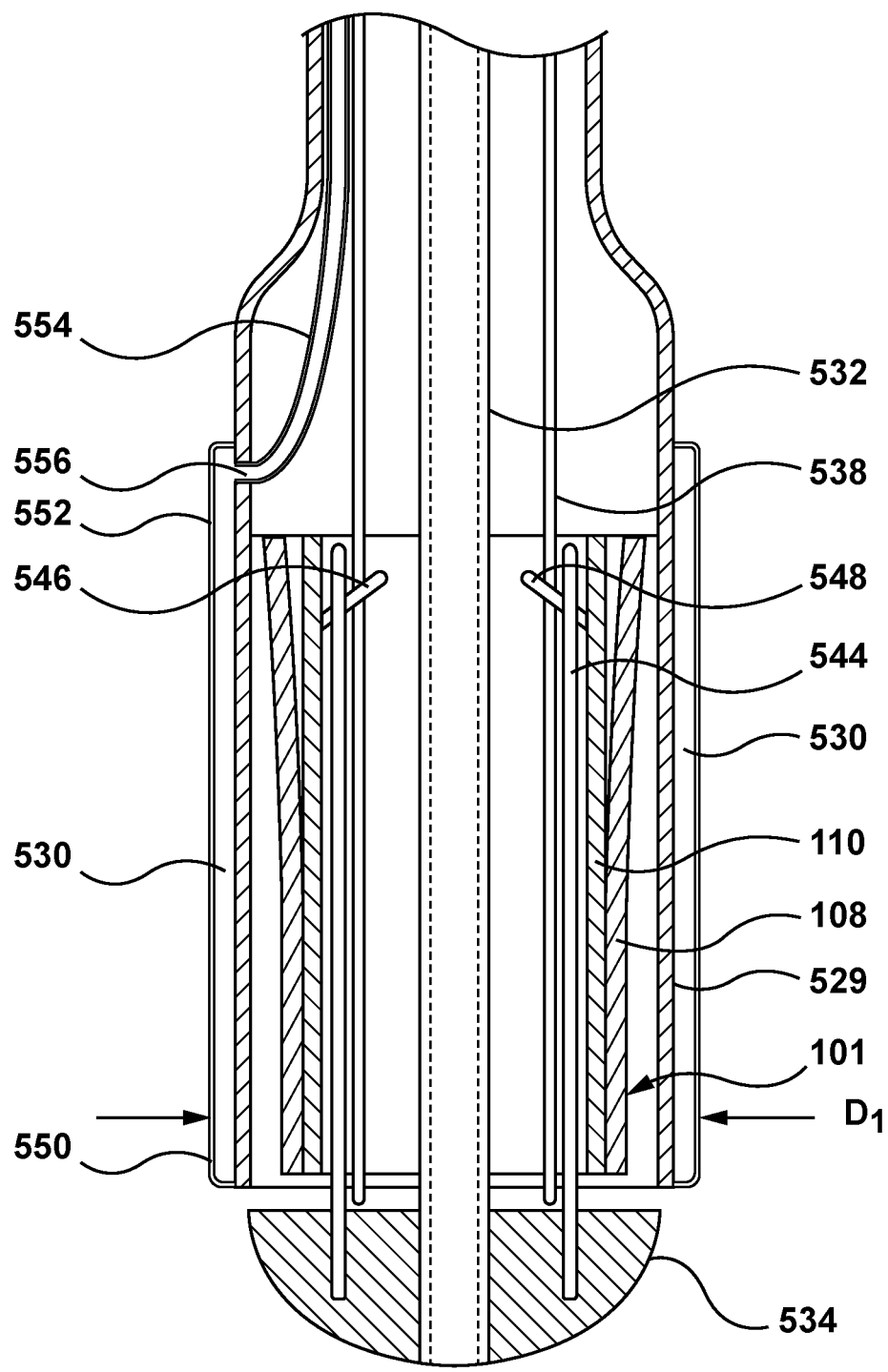
FIG. 6 is an enlarged sectional view of a distal portion of the valve delivery system of FIG. 5, wherein the displacement component is in a delivery or unexpanded state.

Valve delivery catheter 526 is depicted in a delivery configuration in FIGS. 5 and 6 with heart valve prosthesis 101 loaded within a distal delivery sheath or capsule 529 of the delivery system. As shown in FIG. 5A, valve delivery catheter 526 includes a tubular outer shaft 528 defining a lumen 527 there-through and a tubular inner shaft 532 defining a lumen 531 there-through. A nosecone or distal tip 534 is coupled to a distal end of inner shaft 532. Inner shaft 532 is concentrically slideably disposed within lumen 527 of outer shaft 528, and lumen 531 of inner shaft 532 may be sized to slidingly receive a guidewire 536 such that valve delivery catheter 526 may be tracked over the guidewire during delivery of heart valve prosthesis 101. Inner shaft 532 extends through heart valve prosthesis 101 to distal tip 534. Outer shaft 528 extends to delivery sheath or capsule 529 and in the delivery configuration of FIG. 5, delivery sheath or capsule 529 is disposed over heart valve prosthesis 101 to compressively retain heart valve prosthesis 101 in the collapsed or delivery configuration and in crimped engagement with inner shaft 532.

Heart valve prosthesis 101 is coupled to the inner shaft 532 and is releasable from the inner shaft 532 by release wires 538, as more fully described below. Delivery sheath or capsule 529 can protect and secure heart valve prosthesis 101 in its collapsed configuration during delivery. Outer shaft 528 is coupled to a retraction mechanism 540 on a handle 542 of valve delivery catheter 526. Various retraction mechanisms 540 may be used, such as an axially-slidable lever, a rotatable rack and pinion gear, or other known mechanisms. In this way, outer shaft 528 may be retracted relative to inner shaft 532 to release (e.g., deploy) heart valve prosthesis 101 from delivery sheath or capsule 529.

FIG. 6 is an enlarged sectional view showing the distal end of valve delivery catheter 526 with delivery sheath or capsule 529 cut away to illustrate the coupling of heart valve prosthesis 101 to inner shaft 532, which is also described in more detail in U.S. Pat. No. 9,034,032 to McLean et al. previously incorporated by reference in its entirety. A plurality of locking fingers 544 are coupled to nosecone 534 and extend proximally through the interior of valve support 110 of heart valve prosthesis 101. A selected number of posts 102 of valve support 110 of heart valve prosthesis 101 have a coupling element 548 comprising a tab 546 cut out from each post 102 at a proximal end thereof. Tab 546 may be deflected inwardly from the post 102 as shown in FIG. 6 and is configured to extend through a window or opening in locking finger 544. Release or control wires 538 pass through tabs 546, which secure heart valve prosthesis 101 to the inner shaft 532. Release or control wires 538 can be sandwiched tightly between tabs 546 and locking fingers 544, such that friction temporarily prevents release or control wire 538 from slipping in a proximal or distal direction. In this way, delivery sheath or capsule 529 may be retracted relative to heart valve prosthesis 101 to permit expansion of heart valve prosthesis 101 while the inner shaft 532 maintains the longitudinal position of heart valve prosthesis 101 relative to the anatomy. Release or control wires 538 may extend proximally to handle 542, for example, in between inner shaft 532 and outer shaft 528 or within one or more designated lumens. A suitable mechanism (not shown) on handle 542 can allow the operator to retract release or control wires 538 in a proximal direction until they are disengaged from tabs 546. Accordingly, heart valve prosthesis 101 can be released from locking fingers 544 and expand for deployment at the target site.

Figure 7:
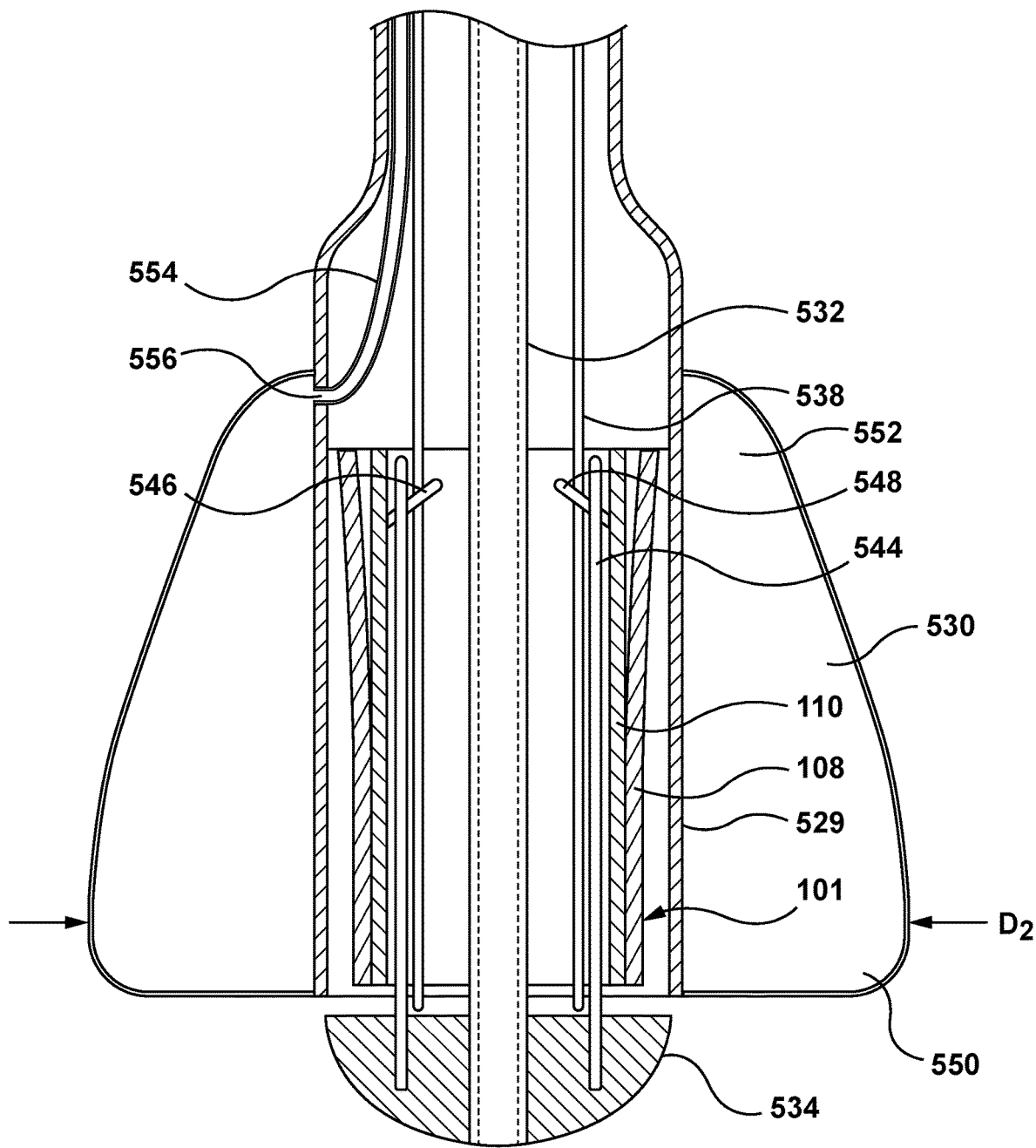
FIG. 7 is an enlarged sectional view of a distal portion of the valve delivery system of FIG. 5, wherein the displacement component is in an expanded or inflated state.
Figure 8:
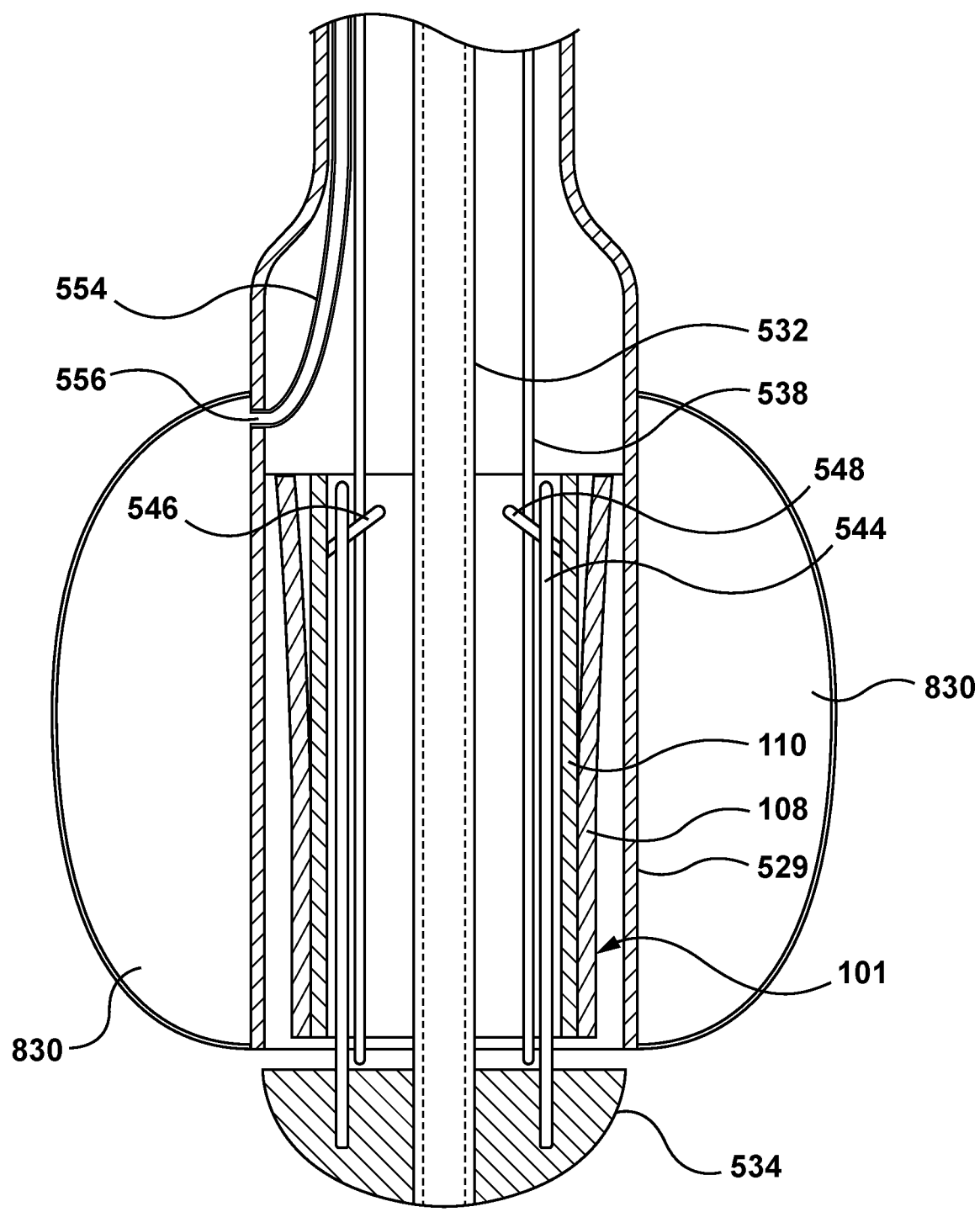
FIG. 8 is an enlarged sectional view of a distal portion of a valve delivery system according to another embodiment hereof, wherein the valve delivery system includes a displacement component which is not tapered and the displacement component is in an expanded or inflated state.

In the embodiment of FIGS. 5-7, displacement component 530 is a balloon coupled to and surrounding an exterior surface of delivery sheath or capsule 529. FIGS. 5 and 6 depict displacement component 530 in its unexpanded or uninflated state, while FIG. 7 illustrates displacement component 530 in its expanded or inflated state. Displacement component 530 is radially expandable between a first outer diameter $D_1$ in its unexpanded or uninflated state and a second outer diameter $D_2$ in its expanded or inflated state. In the unexpanded or uninflated state with first outer diameter $D_1$, the width of displacement component 530 is marginal so as not to increase the overall size and profile of valve delivery catheter 526. As shown in FIG. 7, in its expanded or inflated state with second outer diameter $D_2$, displacement component 530 may have a tapered profile or configuration in which an outer diameter thereof decreases from a distal end 550 to a proximal end 552 thereof. When the outer diameter varies in the expanded or inflated stated, as used herein "second outer diameter" refers to the greatest or largest dimension of the expanded or inflated displacement component unless otherwise stated. In another embodiment depicted in FIG. 8, in its expanded or inflated state, displacement component 830 does not have a tapered profile or configuration. An inflation lumen 554 extends along the length of valve delivery catheter 526 to transmit inflation fluid into displacement component 530 for expansion. In an embodiment hereof, inflation lumen 554 is a single point inflation lumen defined a tubular component that extends along the exterior of inner shaft 532 and/or the interior of outer shaft 528 into proximal end 552 of displacement component 530. In another embodiment hereof (not shown), the inflation lumen may be formed in a sidewall of the outer shaft. Inflation fluid is received through a luer hub 525 (shown on FIG. 5) of handle 542 or other type of fitting that may be connected to a source of inflation fluid to be delivered to displacement component 530.

Proximal and distal ends 552, 550, respectively, of displacement component 530 are sealingly attached to the exterior surface of capsule 529. Adjacent to proximal end 552, displacement component 530 is connected to inflation lumen 554 through an inflation port or opening 556 which is formed through a sidewall of capsule 529. Opening 556 is located proximal to heart valve prosthesis 101 on inner shaft 532 so that integration of inflation lumen 554 and displacement component 530 does not increase the overall profile and size of the delivery catheter.

Displacement component 530 may be made of a polymeric material such as may commonly be used for dilatation balloons, including without limitation PEBAX, Grilimid, nylon in various grades, latex, polyethylene terephthalate (PET), polyamide 12 or polyethylene block amide copolymer. Outer and inner shafts 528, 532 of valve delivery catheter 526 are formed of any suitable flexible polymeric material. Non-exhaustive examples of material for the shaft components are polyethylene terephalate (PET), nylon, polyethylene, PEBAX, or combinations of any of these, either blended or co-extruded. Optionally, a portion of the shaft components is formed as a composite having a reinforcement material incorporated within a polymeric body to enhance strength, flexibility, and/or toughness. Suitable reinforcement layers include braiding, wire mesh layers, embedded axial wires, embedded helical or circumferential wires, and the like. In an embodiment, the proximal portion of outer shaft 528 may in some instances be formed from a metallic tubing, such as a hypotube, or a reinforced polymeric tube as shown and described, for example, in U.S. Pat. No. 5,827,242 to Follmer et al., which is incorporated by reference herein in its entirety. The shaft components may have any suitable working length to extend to a target location within the heart.

Figure 9:
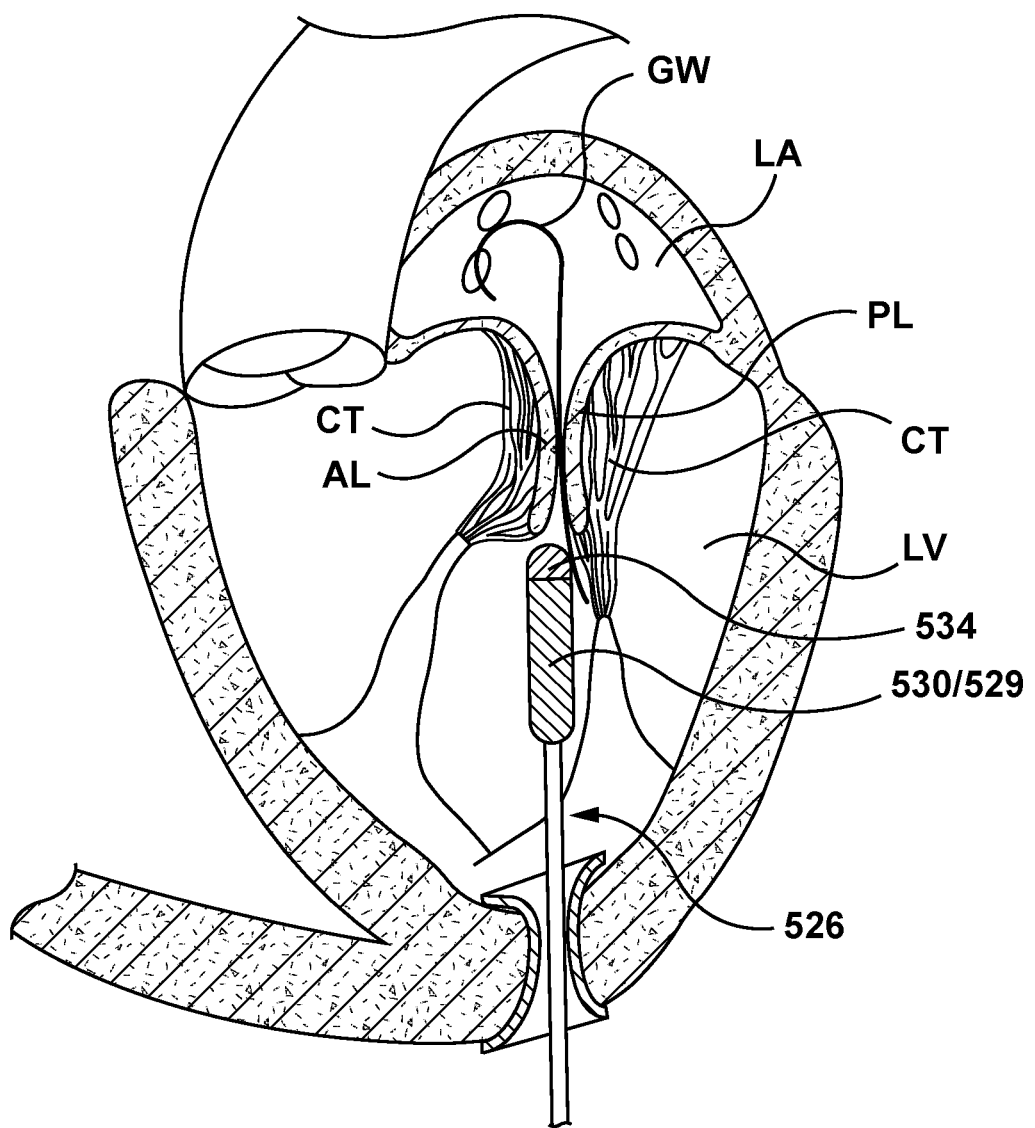
FIG. 9 is an illustration of the valve delivery system of FIG. 5 in situ, the valve delivery system being positioned into the left ventricle via a transapical approach, wherein the displacement component of the valve delivery system is in a delivery or unexpanded configuration.

FIGS. 9-13 are cross-sectional views of a heart showing a method of delivering a heart valve prosthesis 101 to an annulus of a native mitral valve of a heart using a transapical approach in accordance with embodiments hereof. Referring to FIG. 9, valve delivery catheter 526 is advanced over a guidewire GW through guiding catheter GC (not shown) which enters the left ventricle LV of the heart through a puncture in the left ventricle wall at or near the apex of the heart and is sealed by a purse-string suture. Alternatively, valve delivery catheter 526 may be placed directly through a purse-string-sealed transapical incision without a guiding catheter. Valve delivery catheter 526 is positioned into the left ventricle via a transapical approach and positioning valve delivery catheter 526 within the left ventricle of the heart includes introducing the catheter into the apex of the heart as well as introducing the catheter through a ventricular wall adjacent to the apex of the heart. Stated another way, "transapical approach" as used herein is not limited to introduction via only the apex of the heart but also includes the ventricular wall adjacent to the apex of the heart since the anatomy of a heart may vary from patient to patient. Further, as noted above, although described in FIG. 9 as being introduced into the left ventricle for treatment of chordae tendineae associated with a native mitral valve, valve delivery catheter 526 may be similarly introduced into the right ventricle for treatment of chordae tendineae associated with a native tricuspid valve. Heart valve prosthesis 101 is in the delivery or collapsed configuration within capsule 529, and displacement component 530 is in its delivery or unexpanded state in which the displacement component has the first outer diameter $D_1$.

Figure 10:
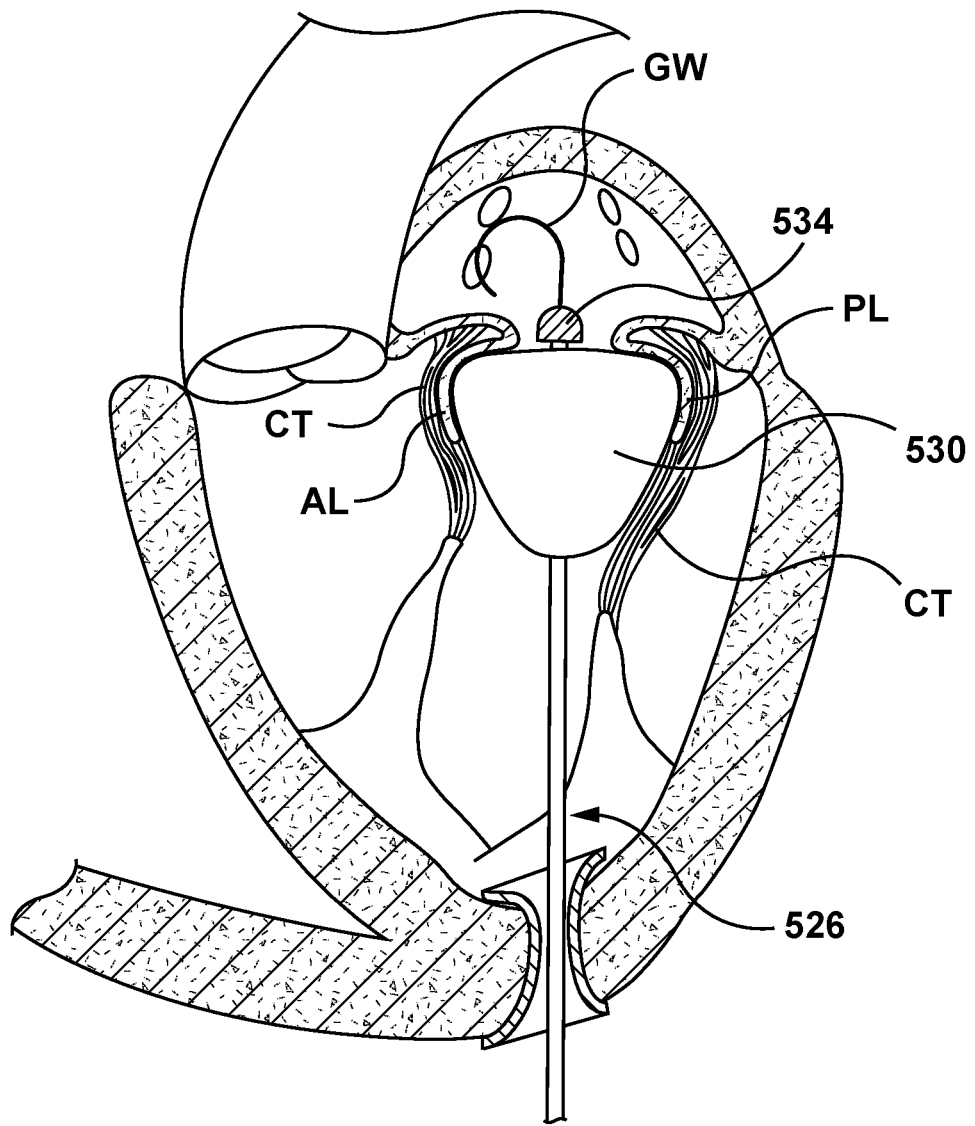
FIG. 10 is an illustration of the valve delivery system of FIG. 5 in situ, wherein the displacement component of the valve delivery system is in a deployed or expanded configuration.

With heart valve prosthesis still in the delivery configuration, displacement component 530 of valve delivery catheter 526 is radially expanded into its expanded or inflated state in which the displacement component has the second outer diameter $D_2$ greater than the first outer diameter $D_1$. Valve delivery catheter 526 is then maneuvered and advanced towards the annulus of the native mitral valve of the heart with displacement component 530 in the expanded or inflated state until displacement component 530 (and delivery sheath or capsule 529 containing collapsed heart valve prosthesis 101) is positioned within the annulus of the native mitral valve between native leaflets AL, PL as shown in FIG. 10. With displacement component 530 inflated, displacement component 530 displaces or pushes all chordae tendineae CT, trabeculae and ventricular bands radially outwards towards the ventricular wall and away from the valve delivery catheter during advancement of valve delivery catheter 526. The second outer diameter $D_2$ of inflated displacement component 530 is of a dimension that prevents the displacement component from passing through openings between chordae in a left ventricle. Displacement of the chordae tendineae CT does not damage the chordae tendineae, but rather provides an unobstructed pathway to the native mitral valve. In an embodiment hereof, displacement component 530 may be inflated with an endoinflater (not shown) as will be understood by one of ordinary skill in the art. Displacement component 530 may be fully inflated or expanded, or may be only partially inflated or expanded as required to push all chordae tendineae, trabeculae and ventricular bands radially outwards towards the ventricular wall. The width and length of displacement component 530 relative to the size of the left ventricle may vary from that depicted in FIG. 10. The dimensions vary according to application and are only required to be configured to push chordae tendineae outwards enough provide to an unobstructed pathway to the native mitral valve, or to be configured to provide feedback to the user that displacement component 530 has become entangled during advancement.

Figure 11:
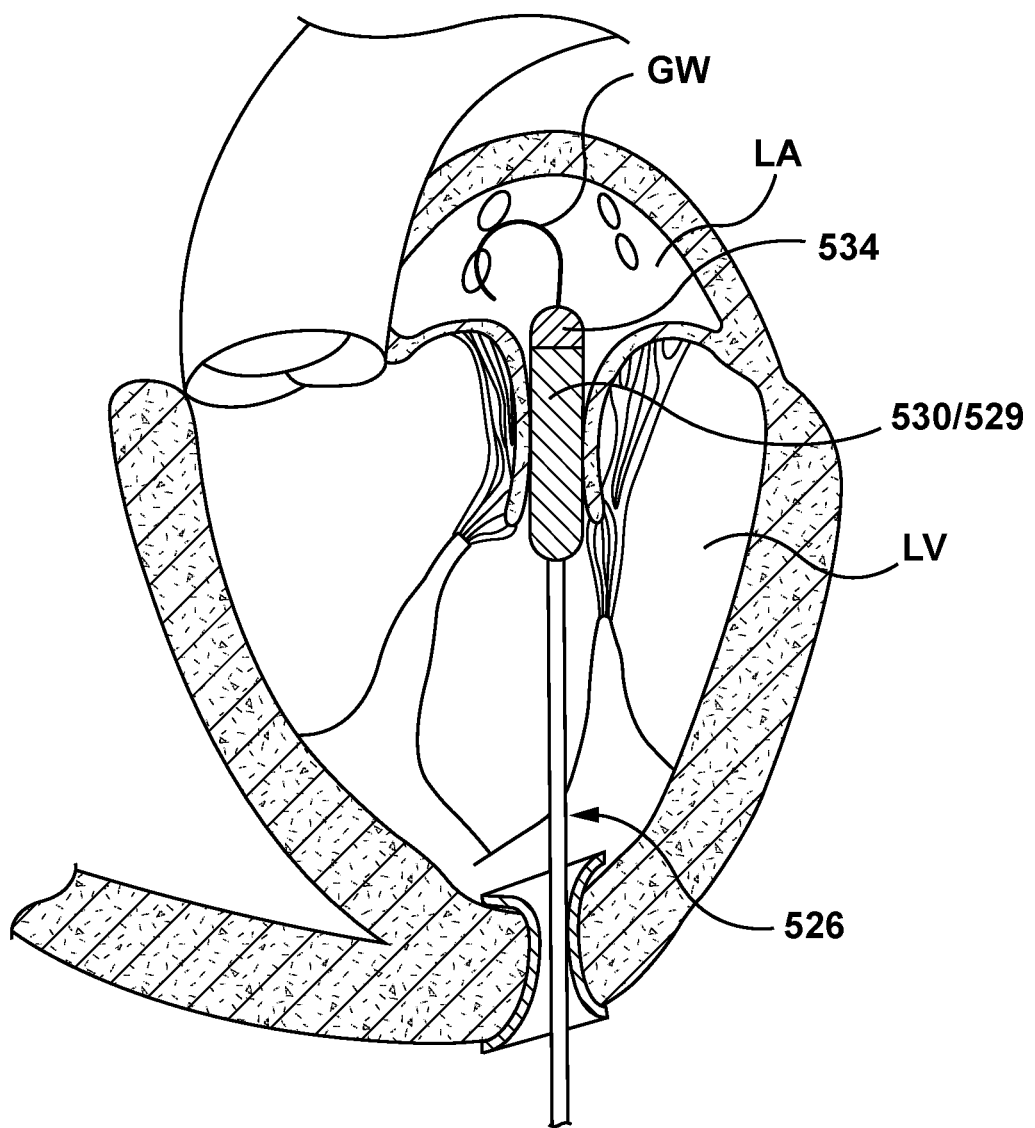
FIG. 11 is an illustration of the valve delivery system of FIG. 5 in situ, wherein the displacement component of the valve delivery system is in at least a partially unexpanded configuration and the valve delivery system has advanced to the native mitral valve.
Figure 12:
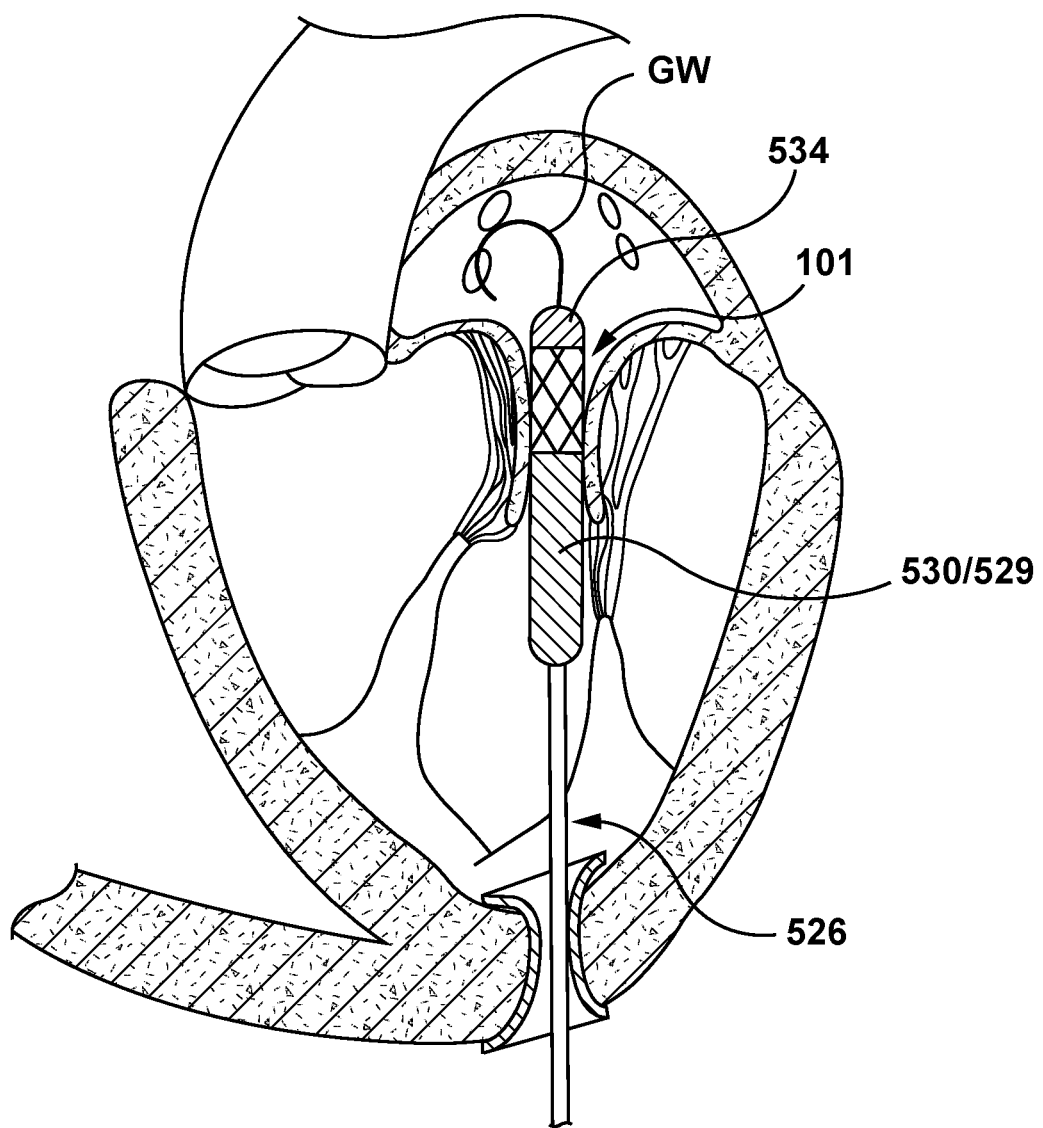
FIG. 12 is an illustration of the valve delivery system of FIG. 5 in situ, wherein a capsule of the valve delivery system is being retracted in order to deploy the valve prosthesis of FIG. 1.
Figure 13:
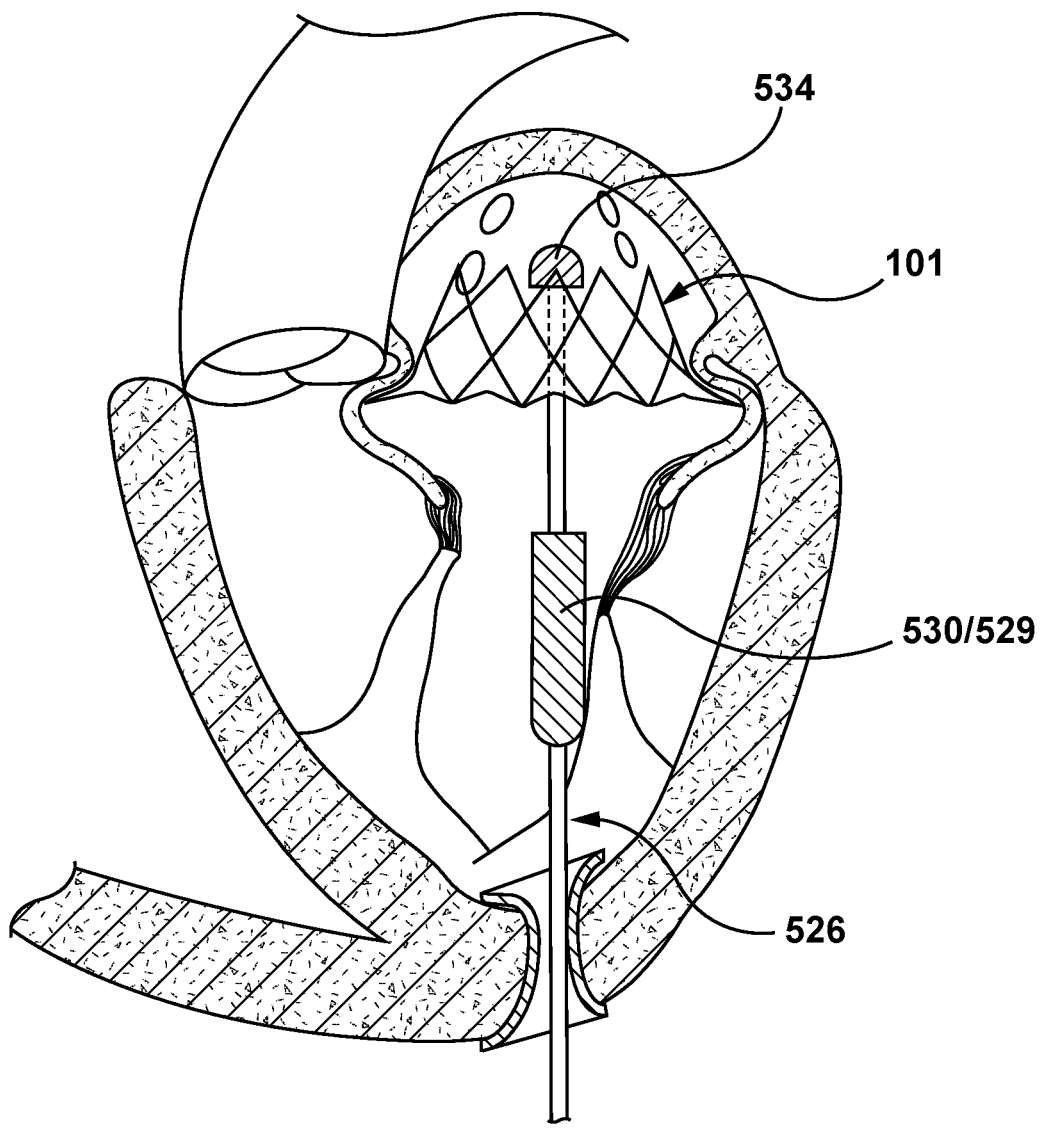
FIG. 13 is an illustration of the valve delivery system of FIG. 5 in situ, wherein a capsule of the valve delivery system has been retracted to deploy the valve prosthesis of FIG. 1 within the native mitral valve.

Once displacement component 530 (and delivery sheath or capsule 529 containing collapsed heart valve prosthesis 101) is positioned within the annulus of the native mitral valve between native leaflets AL, PL, displacement component 530 is at least partially radially collapsed prior to deployment of heart valve prosthesis 101 as shown in FIG. 11. Heart valve prosthesis 101 is then deployed or expanded into apposition with the annulus of the native mitral valve. More particularly, referring to FIG. 12, capsule 529 is proximally retracted to expose and release the entire length of heart valve prosthesis 101. Valve prosthesis 101 self-expands into apposition with the surrounding native anatomy, i.e., with the annulus of the native valve. Release or control wires 538 may be retracted in a proximal direction to release heart valve prosthesis 101 from valve delivery catheter 526, allowing the valve delivery system to be removed and the device to be fully implanted at the native mitral valve in the deployed configuration as shown in FIG. 13. In an embodiment, heart valve prosthesis 101 may be expanded upstream of the desired target location then pulled downstream into the target location before releasing heart valve prosthesis 101 from valve delivery catheter 526. Alternatively, heart valve prosthesis 101 may not be connected to the valve delivery catheter such that heart valve prosthesis 101 deploys and is fully released from valve delivery catheter 526.

In another embodiment hereof, the valve prosthesis is fully deployed prior to deflating displacement component 530. Stated another way, the step of deploying heart valve prosthesis 101 into apposition with the annulus of the native mitral valve occurs with displacement component 530 in the expanded state. More particularly, capsule 529 may be proximally retracted to expose and release the entire length of heart valve prosthesis 101 with displacement component 530 in its inflated state. With displacement component 530 in its inflated state, chordae tendineae CT will be pushed away from the heart valve prosthesis during deployment thereof. Displacement component 530 is then deflated after deployment of the heart valve prosthesis so that valve delivery catheter 526 may be retracted and removed from the patient.

FIGS. 14-15 illustrate another embodiment of a displacement component 1430 that may be used in a valve delivery catheter 1426. Valve delivery catheter is similar to valve delivery catheter 526 described above. However, in this embodiment, displacement component 1430 includes a first balloon 1430A that is coupled to an inner shaft 1432 of the valve delivery catheter and a second balloon 1430B which is similar to displacement component 830 and integrated onto an outer surface of capsule 529. In the unexpanded or uninflated state with a first outer diameter $D_1$ (not shown in FIG. 14 but shown in FIG. 6), the width of first and second balloons 1430A, 1430B, respectively, are marginal so as not to increase the overall size and profile of valve delivery catheter 1426. First balloon 1430A forms the distalmost tip of valve delivery catheter 1426 and thus replaces nosecone or distal tip 534 of valve delivery catheter 526. First balloon 1430A has a generally conical shape when in an inflated state as shown in FIG. 14, with a brim or base 1458 that has a wider outer diameter than a conical portion 1459 that narrows or decreases from a proximal end 1460 to a distal end 1462 thereof. Brim or base 1458 has a second outer diameter $D_2$ which is greater than first outer diameter $D_1$. An inflation lumen 1454A extends along the length of valve delivery catheter 1426 to transmit inflation fluid into first balloon 1430A for expansion. As best shown in FIG. 15, which is a cross-section of inner shaft 1432 removed from the valve delivery catheter for illustrative purposes only, inflation lumen 1454A is formed in a sidewall of the inner shaft. Inflation lumen 1454A may be crescent shaped as shown, although other shapes are suitable as well. Inner shaft 1432 defines guidewire lumen 1431 so that valve delivery catheter 1426 may be tracked over a guidewire. First balloon 1430A is connected to inflation lumen 1454A through an inflation port or opening 1456A formed through a sidewall of inner shaft 1432. Inflation fluid is received through a second luer hub (not shown) of handle 542 or other type of fitting that may be connected to a source of inflation fluid to be delivered to first balloon 1430A.

For second balloon 1454B, an inflation lumen 1454B extends along the length of valve delivery catheter 1426 to transmit inflation fluid into second balloon 1430B for expansion. In an embodiment hereof, inflation lumen 1454B is a single point inflation lumen defined a tubular component that extends along the exterior of inner shaft 1432 and/or the interior of outer shaft 528 into the proximal end of second balloon 1430B. Adjacent to the proximal end thereof, second balloon 1430B is connected to inflation lumen 1454B through an inflation port or opening 1456B formed through a sidewall of capsule 529. Inflation fluid is received through luer hub 525 (not shown in FIG. 14) of handle 542 or other type of fitting that may be connected to a source of inflation fluid to be delivered to second balloon 1430B.

Displacement component 1430 may be used to displace or push all chordae tendineae CT, trabeculae and ventricular bands radially outwards towards the ventricular wall and away from the valve delivery catheter during advancement of valve delivery catheter 1426. As described with respect to FIGS. 9-13 herein, valve delivery catheter 1426 is introduced into a ventricle of the heart through a puncture in the ventricle wall at or near the apex of the heart and is sealed by a purse-string suture. Valve delivery catheter 1426 is positioned into the left ventricle via a transapical approach and positioning valve delivery catheter 1426 within the left ventricle of the heart includes introducing the catheter into the apex of the heart as well as introducing the catheter through a ventricular wall adjacent to the apex of the heart as described above. Heart valve prosthesis 101 is in the delivery or collapsed configuration within delivery the sheath or capsule 529, and displacement component 1430 is in its delivery or unexpanded state in which the displacement component has a first or unexpanded outer diameter $D_1$. With heart valve prosthesis still in the delivery configuration, both first and second balloons 1430A, 1430B, respectively, of displacement component 1430 are radially expanded into their expanded or inflated states in which displacement component 1430 has the second outer diameter $D_2$ greater than the first outer diameter $D_1$. Valve delivery catheter 1426 is then maneuvered and advanced towards the annulus of the native valve of the heart with displacement component 1430 in the expanded state. With displacement component 1430 inflated, displacement component 1430 displaces or pushes all chordae tendineae CT, trabeculae and ventricular bands radially outwards towards the ventricular wall and away from the valve delivery catheter during advancement of valve delivery catheter 1426. The second outer diameter $D_2$ of inflated displacement component 1430 is of a dimension that prevents the displacement component from passing through openings between chordae in a left ventricle. First balloon 1430A of displacement component 1430 creates a path through the chordae tendineae CT for valve delivery catheter 1426 to follow, while second balloon 1430B located around capsule 529 avoids entanglement or hang up of the chordae tendineae CT thereon. Once delivery sheath or capsule 529 containing collapsed heart valve prosthesis 101 is positioned within the annulus of the native mitral valve, displacement component 1430 may be deflated and heart valve prosthesis 101 is then deployed or expanded into apposition with the annulus of the native mitral valve. Alternatively, heart valve prosthesis 101 may be deployed with displacement component 1430 still inflated and first and/or second balloons 1430A, 1430B may be deflated after deployment of the heart valve prosthesis. Further, although depicted with both first and second balloons 1430A, 1430B, displacement component 1430 in another embodiment hereof may include only first balloon 1430A for displacing chordae tendineae CT during advancement of the valve delivery system.

Figure 16:
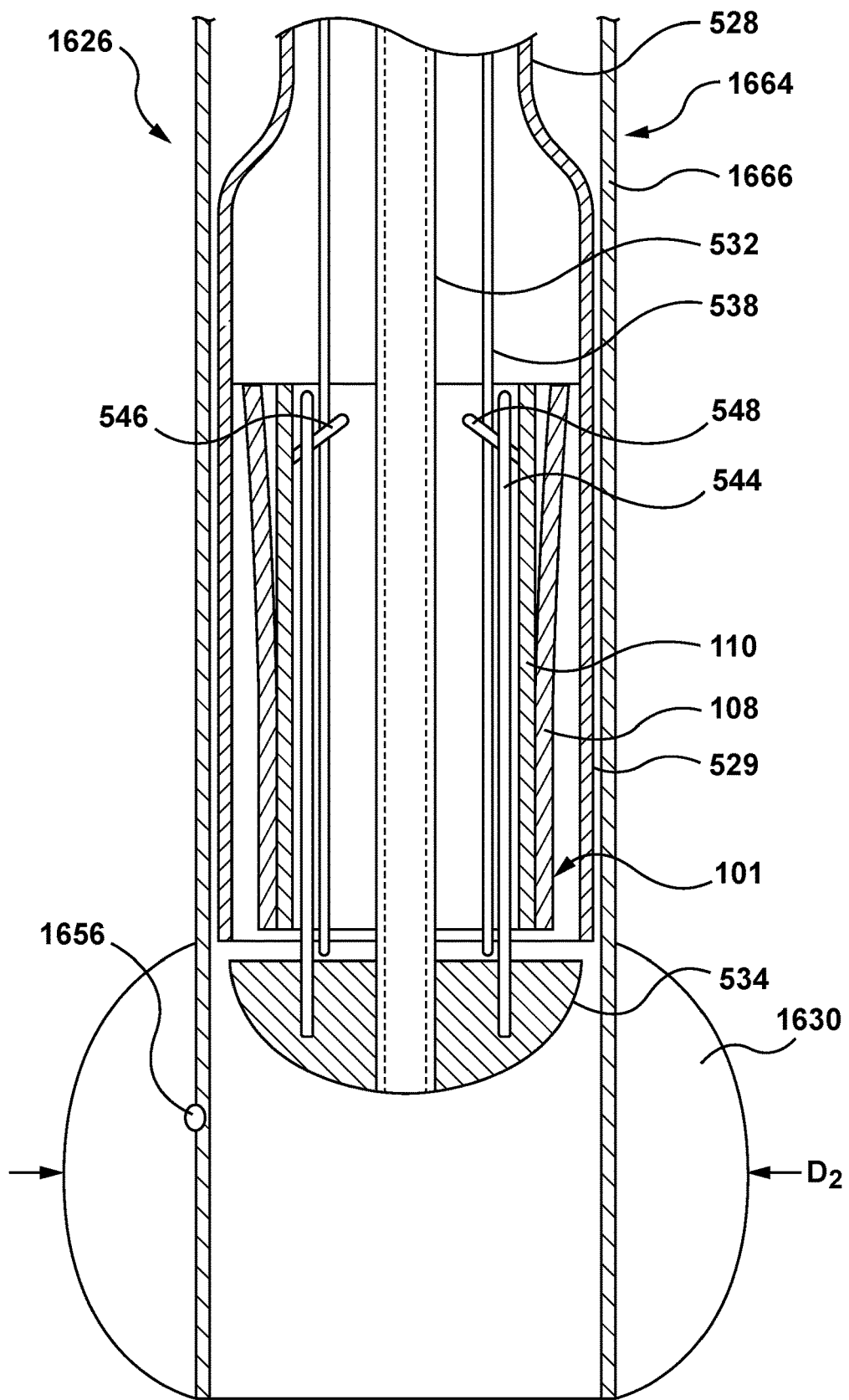
FIG. 16 is an enlarged sectional view of a distal portion of a valve delivery system according to another embodiment hereof, wherein the valve delivery system includes a balloon protection device having a displacement component thereon and the displacement component is in an expanded or inflated state.
Figure 17:
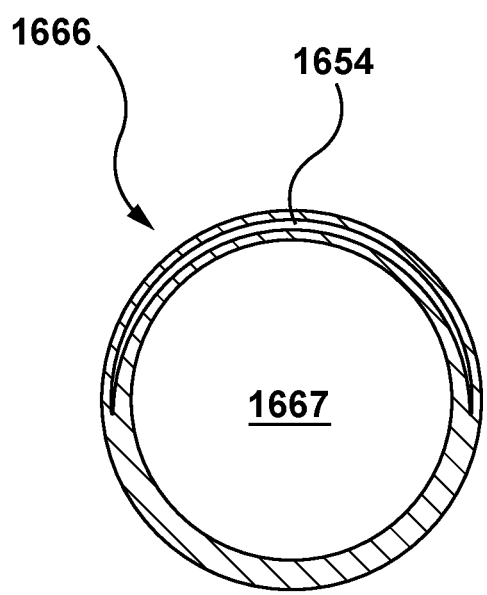
FIG. 17 is a cross-sectional view of an outermost shaft of the balloon protection device of FIG. 16, wherein the outermost shaft is shown removed from the valve delivery system for illustrative purposes only.

FIGS. 16-17 illustrate another embodiment of a displacement component 1630 that may be used in a valve delivery catheter 1626. Valve delivery catheter 1626 is similar to valve delivery catheter 526 described above except that a balloon protection device 1664 is disposed thereover. More particularly, balloon protection device 1664 includes an outermost sheath 1666 that defines a lumen 1667 therethrough and also includes displacement component 1630 at a distal end of outermost sheath 1666. Outer shaft 528 and capsule 529 are disposed within lumen 1667 of outermost sheath 1666. Outermost sheath 1666 is coupled to capsule 529 such that outermost sheath 1666 moves concurrently with valve delivery catheter 1626 as an assembly. Balloon protection device 1664 may be considered an integrated sub-assembly of valve delivery catheter 526. As will be explained in more detail herein, balloon protection device 1664 is temporarily and releasably attached to valve delivery catheter 1626 via a coupling mechanism 3792 (shown in FIGS. 37 and 38) so that balloon protection device 1664 may be selectively detached from valve delivery catheter 1626.

In the embodiment of FIGS. 16-17, displacement component 1630 is a balloon coupled to and surrounding an exterior surface of outermost sheath 1666 of balloon protection device 1664. In the unexpanded or uninflated state with a first outer diameter $D_1$ (not shown in FIG. 16 but shown in FIG. 6), the width of displacement component 1630 is marginal so as not to increase the overall size and profile of valve delivery catheter 1626. Displacement component 1630 is disposed distal to valve prosthesis 101 and also is primarily disposed distal to nosecone 534 of valve delivery catheter 1626 so that displacement component 1630 forms a distalmost tip of valve delivery catheter 1626. An inflation lumen 1654 extends along the length of balloon protection device 1664 to transmit inflation fluid into displacement component 1630 for expansion. As best shown in FIG. 17, which is a cross-section of outermost sheath 1666 removed from the valve delivery catheter for illustrative purposes only, inflation lumen 1654 is formed in a sidewall of outermost sheath 1666. Inflation lumen 1654 may be crescent shaped as shown, although other shapes are suitable as well. Displacement component 1630 is connected to inflation lumen 1654 through an inflation port or opening 1656 which is formed through a sidewall of outermost sheath 1666. Inflation fluid is received through a luer hub (not shown) of a handle disposed outside of the patient or other type of fitting that may be connected to a source of inflation fluid to be delivered to displacement component 1630.

Figure 37:
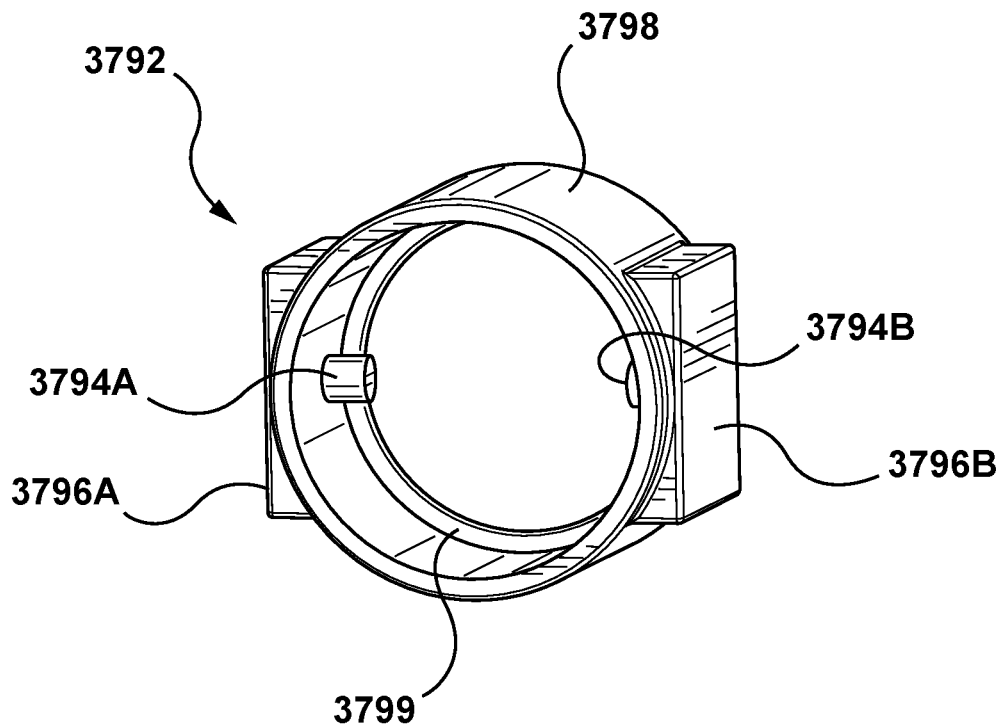
FIG. 37 is a perspective view of a coupling element for use with the embodiment of FIG. 16, wherein pins of the coupling mechanism are in an engaged or coupled configuration.
Figure 38:
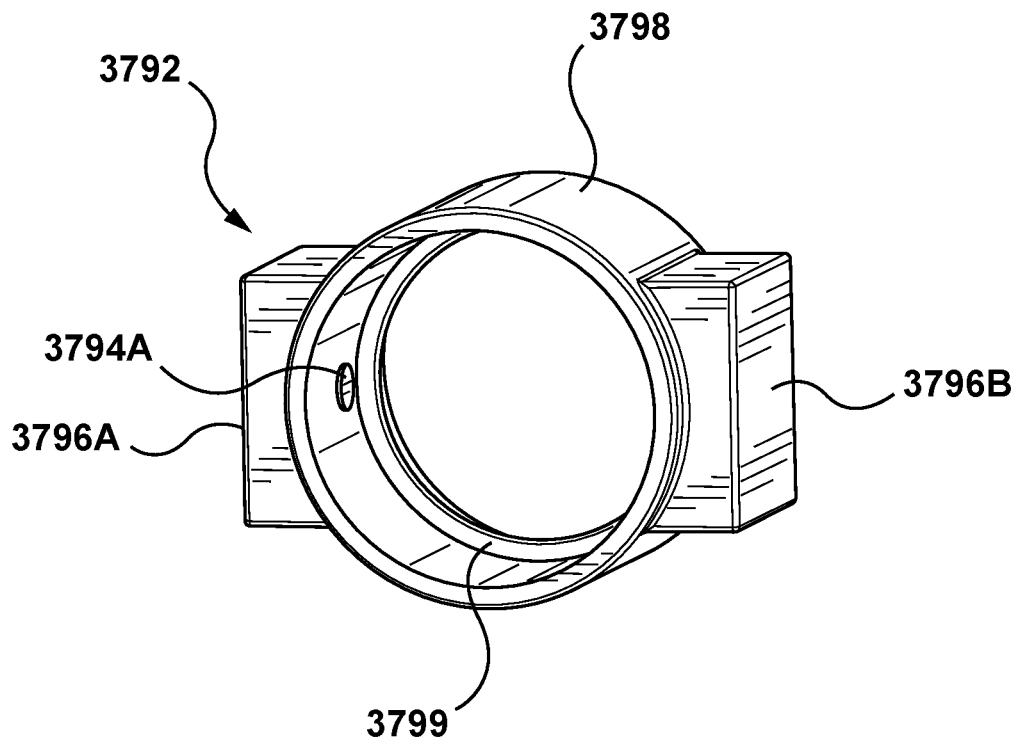
FIG. 38 is a perspective view of the coupling mechanism of FIG. 37, wherein the pins of the coupling mechanism are in a disengaged or uncoupled configuration.

Displacement component 1630 may be used to displace or push all chordae tendineae CT, trabeculae and ventricular bands radially outwards towards the ventricular wall and away from the valve delivery catheter during advancement of valve delivery catheter 1626. As described with respect to FIGS. 9-13 herein, valve delivery catheter 1626, concurrently with balloon protection device 1664, is introduced into a ventricle of the heart through a puncture in the ventricle wall at or near the apex of the heart and is sealed by a purse-string suture. Outermost sheath 1666 of balloon protection device 1664 is initially attached to outer shaft 528 of valve delivery system 1626, and the entire system is advanced together as one. More particularly, with additional reference to FIGS. 37 and 38, coupling mechanism 3792 releasably couples outermost sheath 1666 of balloon protection device 1664 to outer shaft 528 of valve delivery system 1626. Coupling mechanism 3792 includes an annular hub 3798, an O-ring 3799 disposed on an inner surface of hub 3798, two opposing pins 3794A, 3794B, and two opposing user contact buttons 3796A, 3796B. Outer shaft 528 of valve delivery system 1626 includes a first set of two recesses or holes (not shown) formed on the outer surface thereof, just distal to handle 542. Hub 3798 is disposed at a proximal end (not shown) of outermost shaft 1666 of balloon protection device 1664. Hub 3798 is disposed over the first set of two holes of outer shaft 528 so that the coupling mechanism is positioned or disposed over a proximal end of outer shaft 528, just distal to handle 542. Pins 3794A, 3794B slidingly extend through the sidewall of hub 3798. Pins 3794A, 3794B may be manually pushed inwards and pulled outwards in a radial direction via user contact buttons 3796A, 3796B, respectively. When pins 3794A, 3794B are manually pushed radially inwards, they extend or sit within the corresponding first set of holes on outer shaft 528 of valve delivery system 1626 thus temporarily locking or attaching the balloon protection device to the valve delivery system. When pins 3794A, 3794B in the hub of balloon protection device 1664 are manually pulled radially outwards, the balloon protection device is not attached to the valve delivery system and coupling mechanism 3792 may longitudinally slide along the outer surface of outer shaft 528 via O-ring 3799 so that the balloon protection device may be repositioned as described herein. FIG. 37 illustrates pins 3794A, 3794B in an engaged or coupled configuration in which the pins are pushed radially inwards and configured to be disposed within the first set of two holes of outer shaft 528, while FIG. 38 illustrates pins 3794A, 3794B in a disengaged or uncoupled configuration in which the pins are flush with the inner surface of coupling mechanism 3792 and coupling mechanism 3792 is thus no longer attached to outer shaft 528 of valve delivery system 1626.

With pins 3794A, 3794B in an engaged or coupled configuration to temporarily attach the balloon protection device to the valve delivery system, balloon protection device 1664 and valve delivery system 1626 are simultaneously advanced together as one. Valve delivery catheter 1626, concurrently with balloon protection device 1664, is positioned into the left ventricle via a transapical approach and positioning valve delivery catheter 1626 within the left ventricle of the heart includes introducing the catheter into the apex of the heart as well as introducing the catheter through a ventricular wall adjacent to the apex of the heart as described above. Heart valve prosthesis 101 is in the delivery or collapsed configuration within delivery the sheath or capsule 529, and displacement component 1630 of balloon protection device 1664 is in its delivery or unexpanded state in which the displacement component has a first or unexpanded outer diameter $D_1$.

After valve delivery system 1626 and balloon protection device 1664 are positioned within the left ventricle as desired, balloon protection device 1664 is disconnected or detached from valve delivery system 1626. In order to disconnect or detach balloon protection device 1664 from valve delivery system 1626, pins 3794A, 3794B are moved to the disengaged or uncoupled configuration in which the pins are flush with the inner surface of coupling mechanism 3792 and coupling mechanism 3792 is no longer attached to outer shaft 528 of valve delivery system 1626. Pins 3794A, 3794B are moved to the disengaged or uncoupled configuration via user contact buttons 3796A, 3796B, respectively, which breaks the connection between the balloon protection device and the valve delivery system sheath.

After disconnection, balloon protection device 1664 and valve delivery system 1626 are longitudinally movable or slidable relative to one another via O-ring 3799 of coupling mechanism 3792. Balloon protection device 1664 is then distally advanced further into the heart by the physician, independent of valve delivery system 1626. With heart valve prosthesis 101 still in the delivery configuration within valve delivery system 1626, displacement component 1630 of balloon protection device 1664 is radially expanded into its expanded or inflated state in which the displacement component has the second outer diameter $D_2$ greater than the first outer diameter $D_1$, moving the chordae tendinae aside and creating a pathway through which valve delivery system 1626 may pass through. The second outer diameter $D_2$ of inflated displacement component 1630 is of a dimension that prevents the displacement component from passing through openings between chordae in a left ventricle. At this point, balloon protection device 1664 is not advanced any further and is held in place by the physician holding the proximal portion thereof outside the body. Valve delivery system 1626 is then distally advanced through lumen 1667 of balloon protection device 1664, while the balloon protection device remains in place pushing the chordae aside. Once delivery sheath or capsule 529 is positioned within the annulus of the native mitral valve for deployment of heart valve prosthesis 101, balloon protection device 1664 is reconnected to outer shaft 528 of valve delivery system 1626. More particularly, outer shaft 528 includes a second set of two recesses or holes (not shown) formed on the outer surface thereof, distal to the first set of holes, which permit balloon protection device 1664 to be reconnected to outer shaft 528 of valve delivery system 1626. Pins 3794A, 3794B are moved back into the engaged or coupled configuration to re-attach the balloon protection device to the valve delivery system. Balloon protection device 1664 and valve delivery system 1626 can then be concurrently proximally retracted as an assembly to deploy or expand heart valve prosthesis 101 into apposition with the annulus of the native mitral valve. After deployment of heart valve prosthesis 101, balloon protection device 1664 and valve delivery system 1626 are still connected and thus are concurrently proximally retracted to be removed from the body.

In an embodiment, inflation of displacement component 1630 may occur in a pulsative manner. More particularly, the step of radially expanding displacement component 1630 includes repeatedly or systematically inflating displacement component 1630 in a pulsative manner in which displacement component 1630 is inflated for a first time period and displacement component 1630 is slightly or partially deflated for a second time period. Valve delivery system 1626 is maneuvered and advanced towards the annulus of the native mitral valve of the heart during the second time period when displacement component 1630 is at least slightly or partially deflated. As such, full inflation of displacement component 1630 occurs when valve delivery system 1626 is stationary and the chordae tendineae are displaced or pushed out of the way prior to movement of the valve delivery system, thereby allowing valve delivery system 1626 to safely pass through the ventricle without interference from the chordae tendineae.

Figure 18:
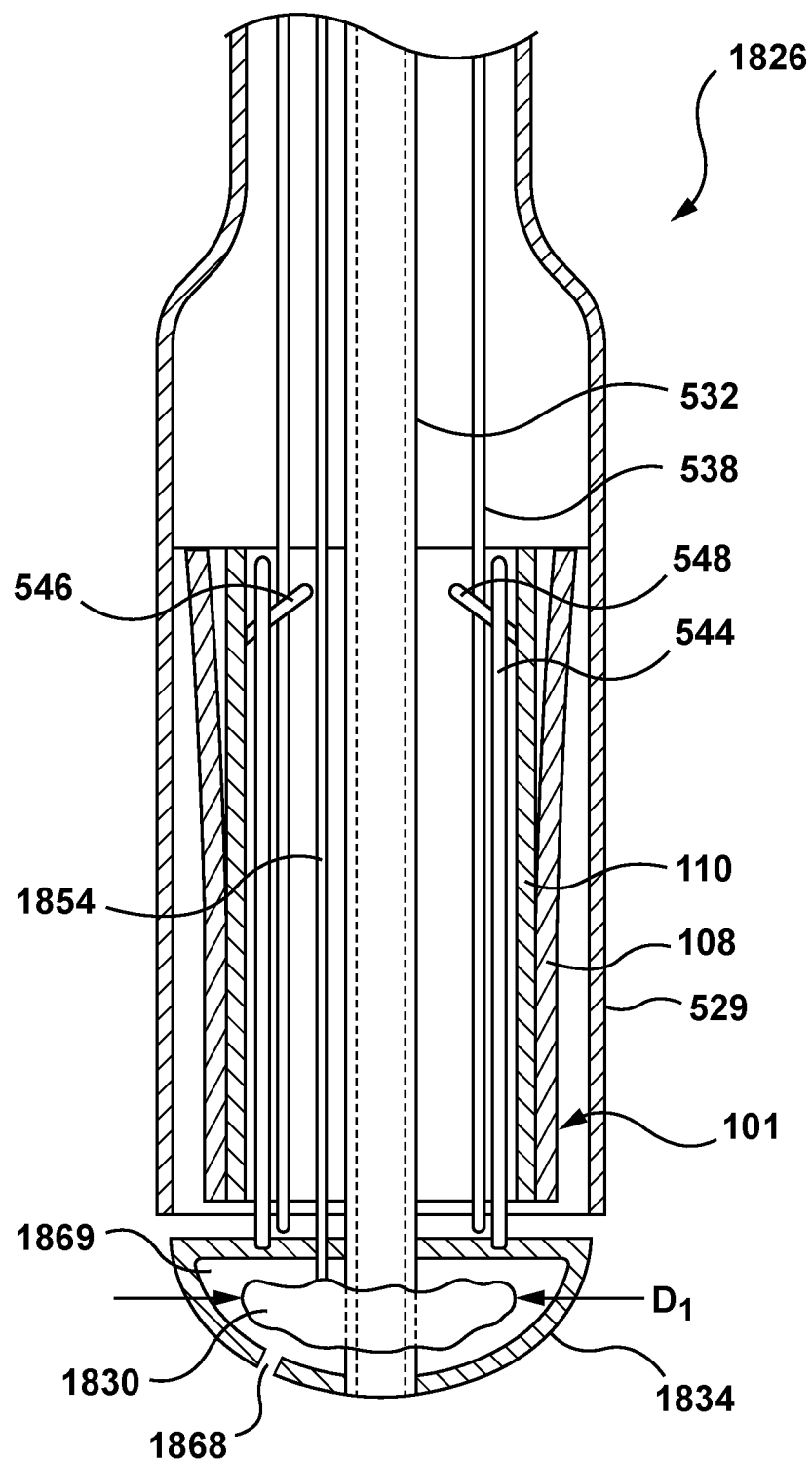
FIG. 18 is an enlarged sectional view of a distal portion of a valve delivery system according to another embodiment hereof, wherein the valve delivery system includes a displacement component which is housed within a hollow distal tip and the displacement component is in an unexpanded or uninflated state.
Figure 19:
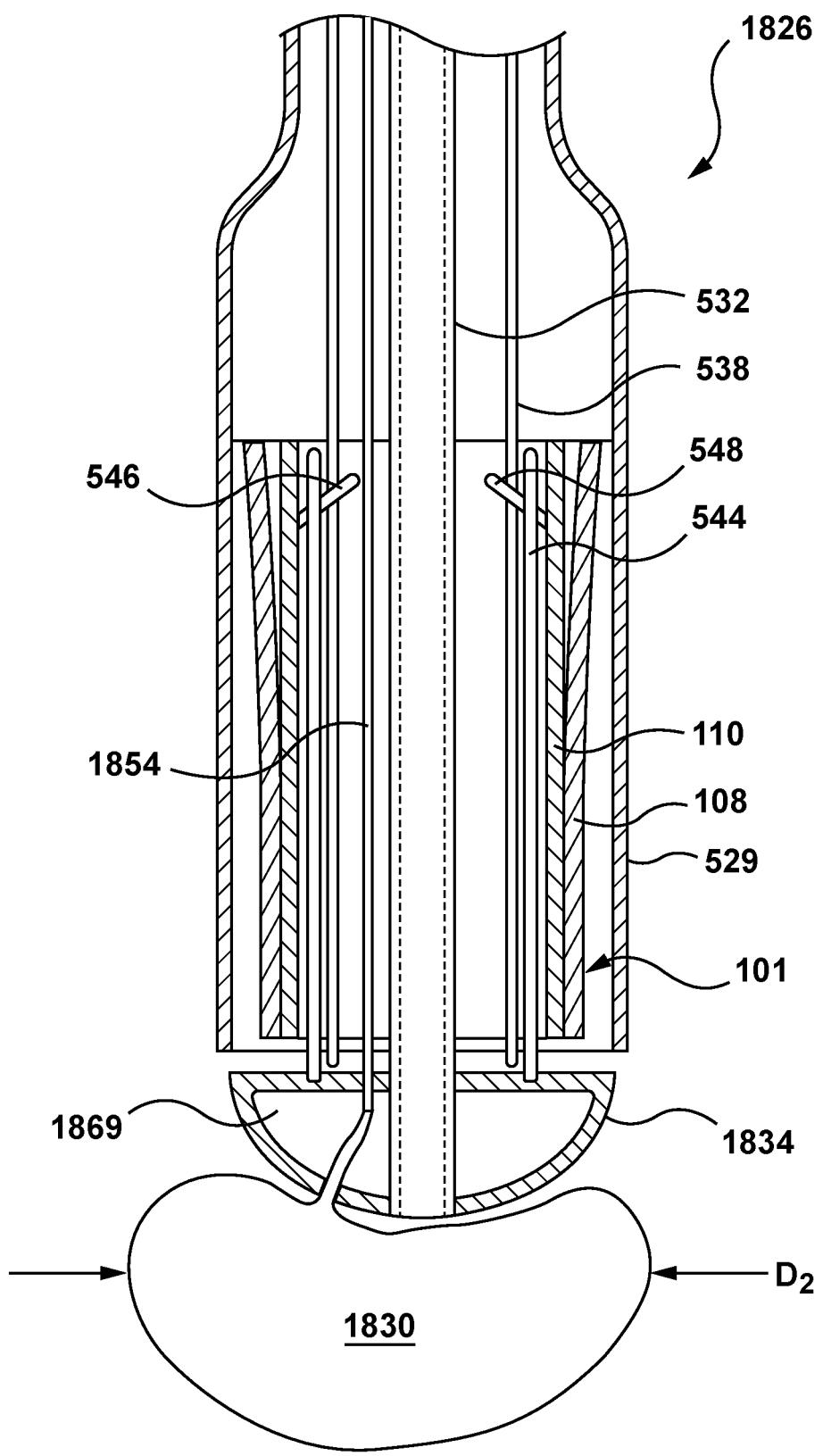
FIG. 19 is an enlarged sectional view of the distal portion of the valve delivery system of FIG. 18, wherein the displacement component is in an expanded or inflated state.

FIGS. 18-19 illustrate another embodiment of a displacement component 1830 that may be used in a valve delivery catheter 1826. Valve delivery catheter 1826 is similar to valve delivery catheter 526 described above except that displacement component 1830 in its unexpanded or uninflated state is housed within a nosecone or distal tip 1834. More particularly, nosecone 1834 is a hollow casing or shell defining a space or chamber 1869. Displacement component 1830 is a balloon coupled to a tubular component that defines an inflation lumen 1854 there-through. Inflation lumen 1854 extends along the length of valve delivery catheter 1826 to transmit inflation fluid into displacement component 1830 for expansion. Inflation lumen 1854 is a single point inflation lumen defined the tubular component that extends along the exterior of inner shaft 532. Displacement component 1830 is disposed at the distal end of the tubular component that defines inflation lumen 1854. Inflation fluid is received through luer hub 525 (not shown in FIG. 18) of handle 542 or other type of fitting that may be connected to a source of inflation fluid to be delivered to displacement component 1830.

In the unexpanded or uninflated state shown in FIG. 18, displacement component 1830 has a first outer diameter $D_1$ is housed or disposed within chamber 1869 defined by nosecone 1834 to thereby provide the displacement component with its delivery state. Displacement component 1830 in the unexpanded or uninflated state has a second outer diameter $D_2$ and extends around inner shaft 532 which extends through the center of nosecone 1834. In the expanded or inflated state shown in FIG. 19, displacement component 1830 extends through an opening or port 1868 formed through nosecone 1834 to deploy outside of chamber 1869 and nosecone 1834 to thereby provide the displacement component with its expanded state.

Displacement component 1830 may be used to displace or push all chordae tendineae CT, trabeculae and ventricular bands radially outwards towards the ventricular wall and away from the valve delivery catheter during advancement of valve delivery catheter 1826. As described with respect to FIGS. 9-13 herein, valve delivery catheter 1826 is introduced into a ventricle of the heart through a puncture in the ventricle wall at or near the apex of the heart and is sealed by a purse-string suture. Valve delivery catheter 1826 is positioned into the left ventricle via a transapical approach and positioning valve delivery catheter 1826 within the left ventricle of the heart includes introducing the catheter into the apex of the heart as well as introducing the catheter through a ventricular wall adjacent to the apex of the heart as described above. Heart valve prosthesis 101 is in the delivery or collapsed configuration within delivery the sheath or capsule 529, and displacement component 1830 is in its delivery or unexpanded state in which the displacement component has a first or unexpanded outer diameter $D_1$ and is housed or disposed within chamber 1869 of nosecone 1834. With heart valve prosthesis 101 still in the delivery configuration, displacement component 1830 is radially expanded through port 1868 formed through nosecone 1834 into its expanded or inflated state in which the displacement component has the second outer diameter $D_2$ greater than the first outer diameter $D_1$ and is disposed outside of chamber 1869 and nosecone 1834. Valve delivery catheter 1826 is then maneuvered and advanced towards the annulus of the native valve of the heart with displacement component 1830 in the expanded state. With displacement component 1830 inflated and disposed outside of nosecone 1834, displacement component 1830 displaces or pushes all chordae tendineae CT, trabeculae and ventricular bands radially outwards towards the ventricular wall and away from the valve delivery catheter during advancement of valve delivery catheter 1826. The second outer diameter $D_2$ of inflated displacement component 1830 is of a dimension that prevents the displacement component from passing through openings between chordae in a left ventricle. Once delivery sheath or capsule 529 containing collapsed heart valve prosthesis 101 is positioned within the annulus of the native mitral valve, displacement component 1830 may be deflated and heart valve prosthesis 101 is then deployed or expanded into apposition with the annulus of the native mitral valve. When deflated, displacement component 1830 may retract or return back into chamber 1869 of nosecone 1834 due to a suction force created by removal of the inflation fluid from the interior of displacement component 1830. In another embodiment, displacement component 1830 may remain external or outside of nosecone 1834 after deflation. Alternatively, heart valve prosthesis 101 may be deployed with displacement component 1830 still inflated.

FIGS. 20-21 illustrate another embodiment of a displacement component 2030 that is similar to displacement component 1830. In this embodiment, displacement component 2030 in its unexpanded or uninflated state is housed within a nosecone or distal tip 1834 but is coupled to and surrounds an exterior surface of a distal end of an inner shaft 2032, which is slidingly disposed within outer shaft 528 and capsule 529. As best shown in FIG. 21, which is a cross-section of inner shaft 2032 removed from a valve delivery catheter 2026 for illustrative purposes only, inflation lumen 2054 is formed in a sidewall of the inner shaft. Inflation lumen 2054 may be crescent shaped as shown, although other shapes are suitable as well. Inner shaft 2032 defines guidewire lumen 2031 so that valve delivery catheter 2026 may be tracked over a guidewire. Displacement component 2030 is connected to inflation lumen 2054 through an inflation port or opening 2056 which is formed through a sidewall of inner shaft 2032. Inflation fluid is received through luer hub 525 (not shown in FIG. 20) of handle 542 or other type of fitting that may be connected to a source of inflation fluid to be delivered to displacement component 2030.

Similar to nosecone 1834, nosecone 2034 is a hollow casing or shell defining a space or chamber 2069. In the unexpanded or uninflated state shown in FIG. 20, displacement component 2030 has a first outer diameter $D_1$ is housed or disposed within chamber 2069 defined by nosecone 2034 to thereby provide the displacement component with its delivery state. When it is desired to expand or inflate displacement component 2030, inner shaft 2032 is slidingly distally advanced as indicated by directional arrow 2070 through an opening or port 2068 formed in nosecone 2034 until displacement component 2030 is disposed outside of or external to nosecone 2034. Once displacement component 2030 is external to nosecone 2034, displacement component 2030 may be inflated to an expanded or inflated state similar to that shown in FIG. 18. Similarly, when it is desired to deflate displacement component 2030, displacement component 2030 is deflated and then inner shaft 2032 is slidingly proximally retracted through opening or port 2068 formed in nosecone 2034 until the deflated displacement component 2030 is disposed within nosecone 2034.

FIGS. 22-26 illustrate another embodiment of a displacement component 2230 that may be used in a valve delivery catheter 2226. Valve delivery catheter 2226 is similar to valve delivery catheter 526 described above except that displacement component 2230 is a radially expandable distal tip that is coupled to a distal end of an inner shaft 2232. More particularly, as best shown in FIG. 23, which is a cross-section of inner shaft 2232 removed from the valve delivery catheter for illustrative purposes only, a pullwire lumen 2278 is formed in a sidewall of the inner shaft for slidably receiving a pullwire 2280. A proximal end (not shown) of pullwire 2280 extends to handle 542 outside of the patient and actuating mechanism (not shown) is provided thereon for pushing and/or pulling pullwire 2280 as will be understood by one of ordinary skill in the art. Pullwire 2280 functions to radially deploy and/or collapse displacement component 2230 as will be explained in more detail herein. Inner shaft 2232 defines guidewire lumen 2231 so that valve delivery catheter 2226 may be tracked over a guidewire.

Figure 24:
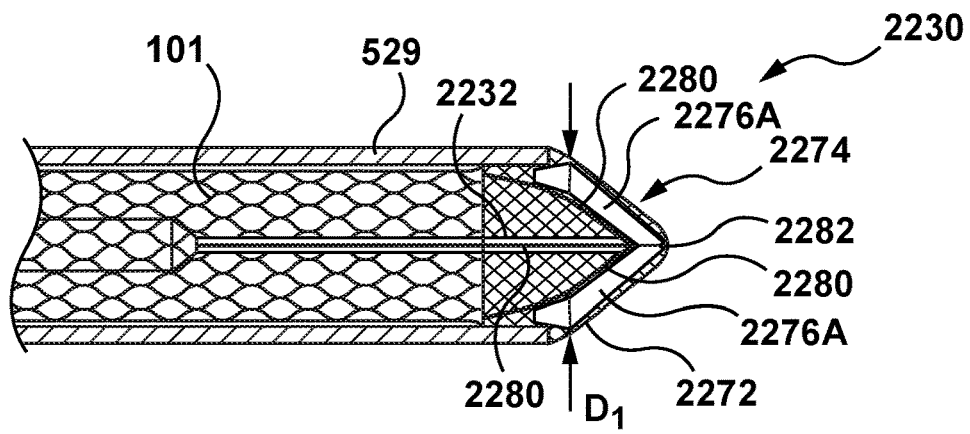
FIG. 24 is a side sectional view of the valve delivery system of FIG. 22, wherein the displacement component is in an unexpanded or delivery state.
Figure 26:
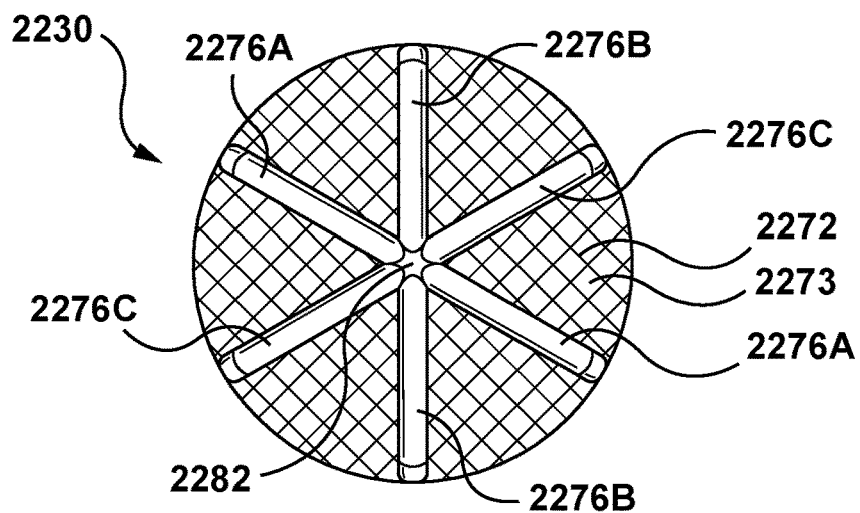
FIG. 26 is an end view of the displacement element of the valve delivery system of FIG. 22, wherein the displacement component is in an expanded or deployed state and the displacement element is shown removed from the valve delivery system for illustrative purposes only.

With additional reference to FIG. 26, displacement component 2230 includes a plurality of spokes 2276A, 2276B, 2276C (collectively referred to as spokes 2276) and a planar or flat component 2272 attached to the plurality of articulating arms or spokes 2276. Spokes 2276A, 2276B, 2276C intersect each other at a centerpoint of each spoke as best shown in FIG. 26. Collectively, spokes 2276 form a support frame 2274 for planar component 2272 and provide structural support for the planar component. Each spoke 2276 is formed from a self-expanding material. In an embodiment shown in FIG. 13, support frame 2274 is self-expanding meaning it has a mechanical memory to return to a pre-set configuration. Mechanical memory may be imparted to the spokes 2276 that form support frame 2274 by thermal treatment to achieve a spring temper in stainless steel, for example, or to set a shape memory in a susceptible metal alloy, such as nitinol. Each spoke 2276 has a joint 2282 at a centerpoint thereon which allows the spoke to bend and collapse into a delivery configuration as shown in FIG. 22 and FIG. 24. To attach or join spokes 2276 to inner shaft 2232, a pin (not shown) may extend through each joint 2282 to couple the spoke to the inner shaft and also permit the spokes to rotate relative to the pin.

In a first embodiment, spokes 2276 are shape set or have a mechanical memory to return to the collapsed or delivery configuration thereof. In this first embodiment, pullwire 2280 applies tension on spokes 2276 in order to cause them to rise and deploy. When the tension is released, the mechanical memory thereof pulls spokes 2276 to its collapsed or delivery configuration shown in FIG. 22 and FIG. 24. In a second embodiment hereof, spokes 2276 are shape set or have a mechanical memory to return to the expanded or deployed configuration thereof. In this second embodiment, pullwire 2280 applies tension on spokes 2276 in order to hold them in the delivery or collapsed configuration of FIG. 22. When the tension is released, the mechanical memory thereof pulls spokes 2276 to their deployed or expanded configuration shown in FIG. 25 and FIG. 26. In both embodiments, pullwire 2280 provides an ability to counter the mechanical memory configuration so that the user may selectively apply a force to expand and also a counter force to collapse displacement component 2230.

Planar component 2272 is a disc and is attached to support frame 2274 to extend over a distalmost surface of spokes 2276. Planar component 2272 is an expandable mesh or braid component formed of a permeable material in order to allow blood to flow there-through. For example, planar component 2272 may be formed from a braided structure constructed from a plurality of metallic wires or filaments woven together or a stamped mesh defining a plurality of open spaces 2273. Open spaces 2273 defined by the mesh when planar component 2272 is expanded allow blood or other fluid to flow there-through during the valve replacement/repair procedure such that the blood flow is not blocked or occluded.

In the unexpanded or delivery state shown in the side views of FIG. 22 and FIG. 24, each spoke 2276 is bent at its respective joint 2282 and at least the unattached ends of each spoke 2276 are disposed within capsule 529 of valve delivery system 2226. Pullwire 2280 extends through inner shaft 2232 via pullwire lumen 2278, and then extends to and is attached to each unattached end of each spoke 2276 as shown in FIG. 24. In the expanded or deployed state shown in the side view of FIG. 25 and the end view of FIG. 26, the plurality of spokes 2276 radially expand such that they are disposed outside of capsule 529. In order to expand or deploy spokes 2276, pullwire 2280 is proximally withdrawn or pulled to cause spokes 2276 to radially expand similar to an umbrella. When pullwire 2280 is pulled back, the portions of pullwire 2280 that extend to each unattached end of each spoke 2276 are forced in a distal direction and thereby spokes 2276 radially expand as indicated by directional arrows 2281 in FIG. 25. When in the expanded or deployed state, each spoke 2276 is substantially straight and is no longer bent at its respective joint 2282.

Figure 27:
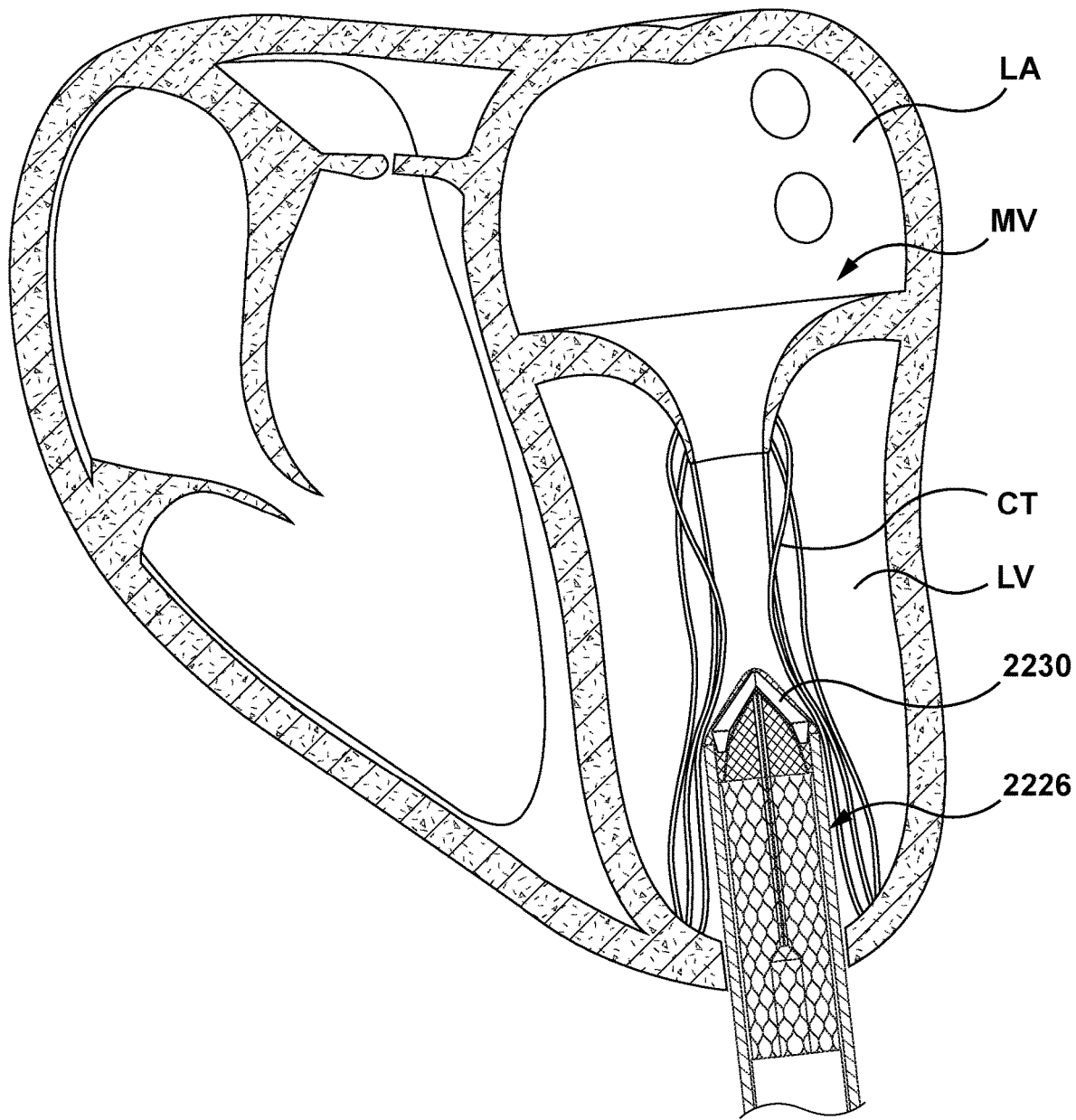
FIG. 27 is an illustration of the valve delivery system of FIG. 22 in situ, the valve delivery system being positioned into the left ventricle via a transapical approach, wherein the displacement component of the valve delivery system is in a delivery or unexpanded configuration.

Displacement component 2230 may be used to displace or push all chordae tendineae CT, trabeculae and ventricular bands radially outwards towards the ventricular wall and away from the valve delivery catheter during advancement of valve delivery catheter 2226. More particularly, with reference to FIG. 27, valve delivery catheter 2226 is introduced into a ventricle of the heart through a puncture in the ventricle wall at or near the apex of the heart and is sealed by a purse-string suture. Valve delivery catheter 2226 is positioned into the left ventricle via a transapical approach and positioning valve delivery catheter 2226 within the left ventricle of the heart includes introducing the catheter into the apex of the heart as well as introducing the catheter through a ventricular wall adjacent to the apex of the heart as described above. Heart valve prosthesis 101 is in the delivery or collapsed configuration within delivery the sheath or capsule 529, and displacement component 2230 is in its delivery or unexpanded state in which the displacement component has a first or unexpanded outer diameter $D_1$, and each spoke 2276 is bent at its respective joint 2282 and at least the unattached ends of each spoke 2276 are disposed within capsule 529 of valve delivery system 2226.

Figure 25:
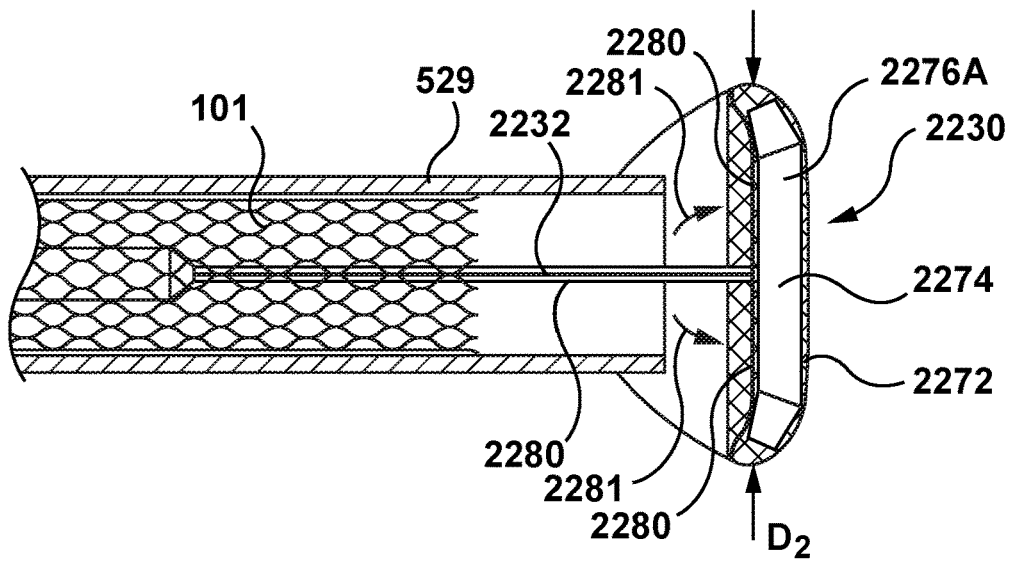
FIG. 25 is a side sectional view of the valve delivery system of FIG. 22, wherein the displacement component is in an expanded or deployed state.

With heart valve prosthesis 101 still in the delivery configuration, displacement component 2230 is radially expanded by manipulation of pullwire 2280. More particularly, if spokes 2276 of displacement component 2230 are shape set or have a mechanical memory to return to the collapsed or delivery configuration thereof, tension on pullwire 2280 is applied in order to cause spokes 2276 to rise and radially expand similar to an umbrella such that spokes 2276 are disposed outside of capsule 529. If spokes 2276 of displacement component 2230 are shape set or have a mechanical memory to return to the expanded or deployed configuration thereof, tension on pullwire 2280 is released in order to permit spokes 2276 to resume their expanded or deployed configuration as shown in FIGS. 25 and 26. As shown on the partial perspective view of FIG. 29, when deployed, each spoke 2276 is substantially straight and is no longer bent at its respective joint 2282 when displacement component 2230 is expanded or deployed.

Figure 28:
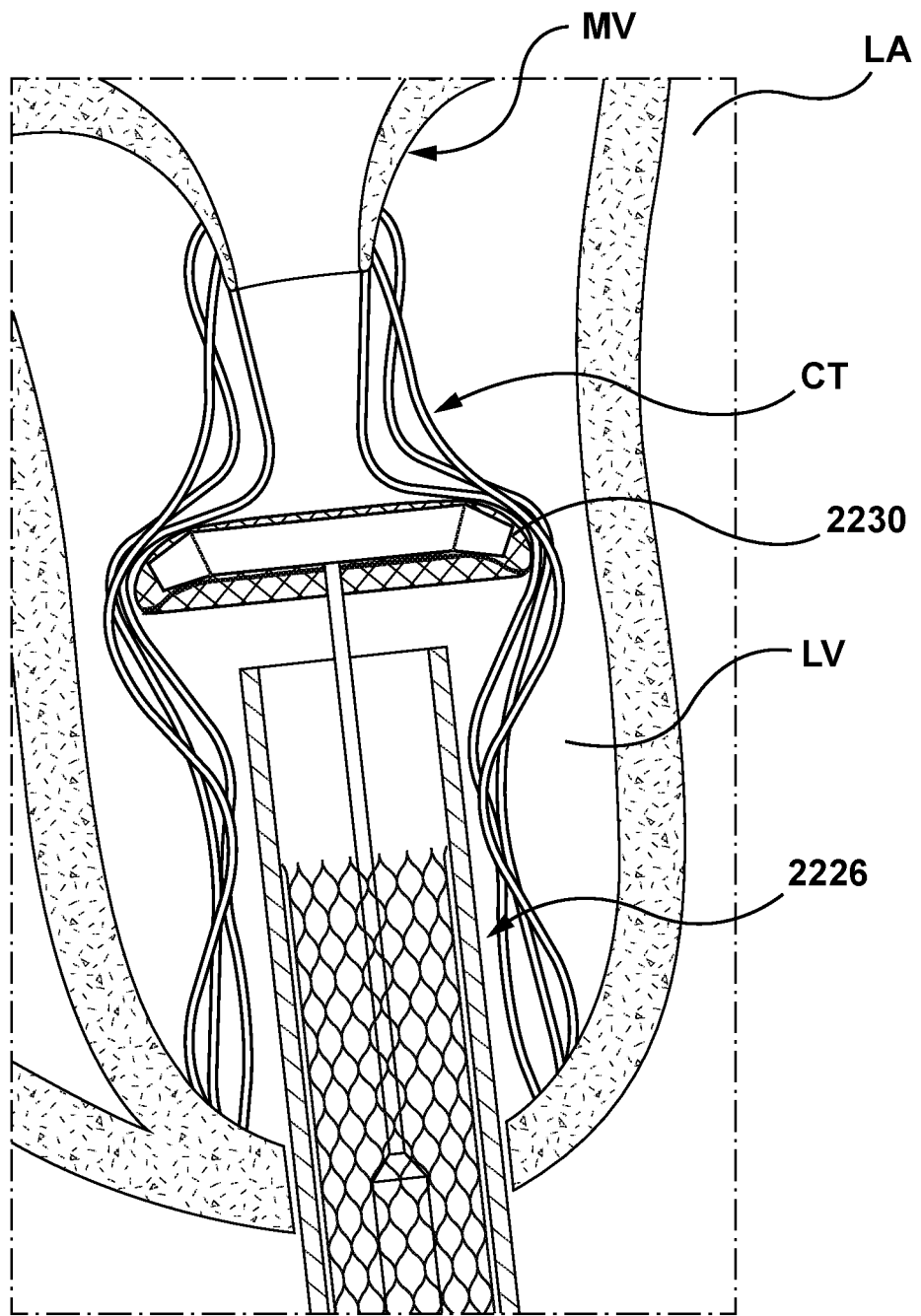
FIG. 28 is an illustration of the valve delivery system of FIG. 22 in situ, wherein the displacement component of the valve delivery system is in a deployed or expanded configuration.
Figure 29:
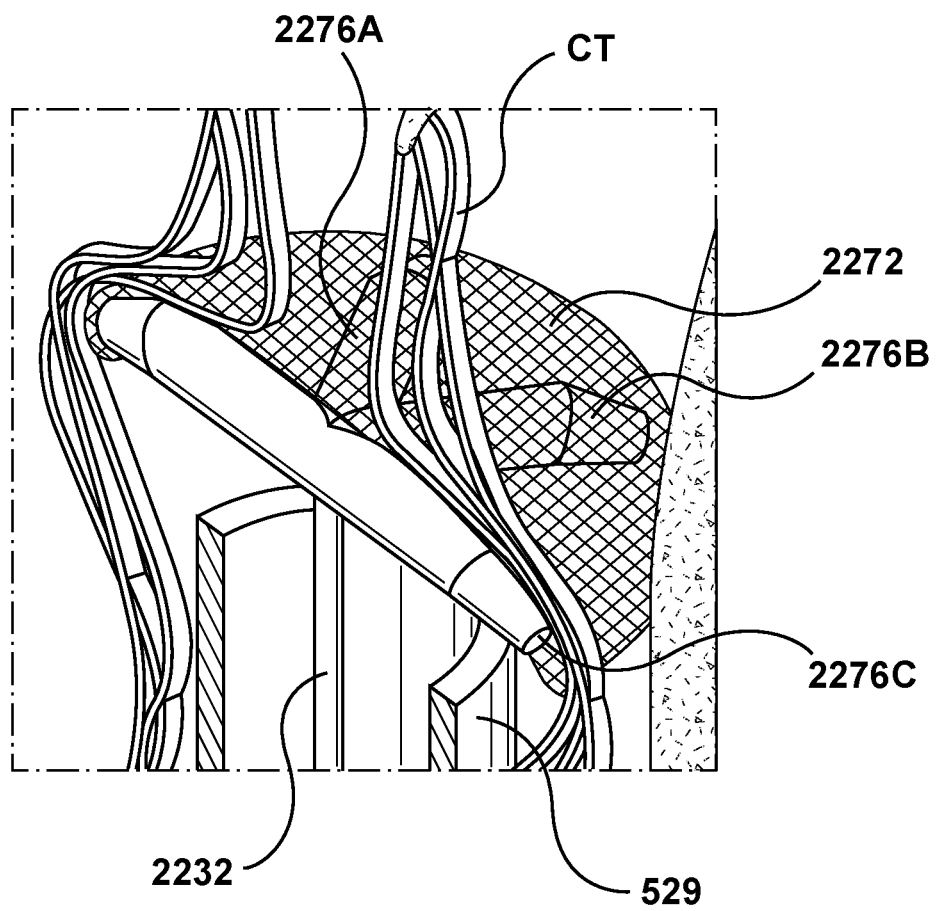
FIG. 29 is a partial perspective view of the valve delivery system of FIG. 22 in situ, wherein the displacement component of the valve delivery system is in a deployed or expanded configuration.

Valve delivery catheter 2226 is then maneuvered and advanced towards the annulus of the native valve of the heart with displacement component 2230 in the expanded state. With displacement component 2230 expanded and disposed outside of capsule 529, displacement component 2230 displaces or pushes all chordae tendineae CT, trabeculae and ventricular bands radially outwards towards the ventricular wall and away from the valve delivery catheter during advancement of valve delivery catheter 2226 as shown in FIGS. 28-29. When expanded, displacement component 2230 has the second outer diameter $D_2$ greater than the first outer diameter $D_1$. The second outer diameter $D_2$ of expanded displacement component 2230 is of a dimension that prevents the displacement component from passing through openings between chordae in a left ventricle.

Figure 30:
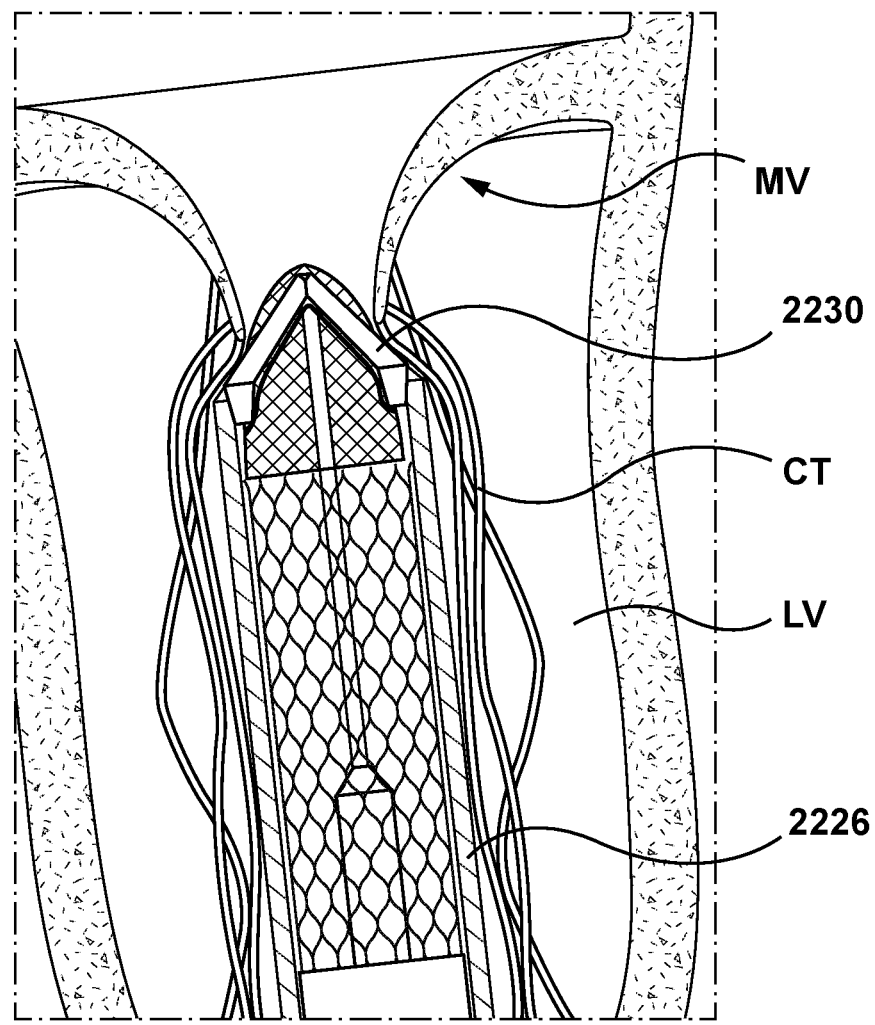
FIG. 30 is an illustration of the valve delivery system of FIG. 22 in situ, wherein the displacement component of the valve delivery system is collapsed and the valve delivery system has advanced to the native mitral valve.
Figure 31:
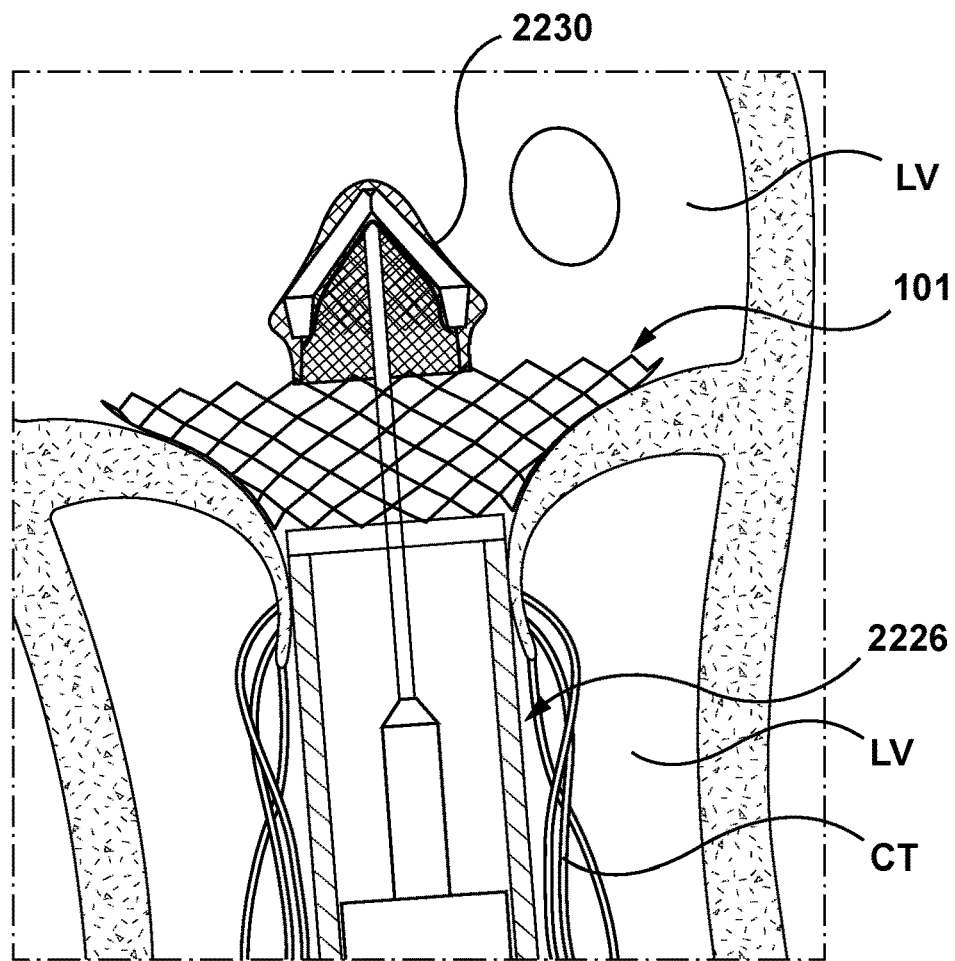
FIG. 31 is an illustration of the valve delivery system of FIG. 22 in situ, wherein a capsule of the valve delivery system has been retracted to deploy the valve prosthesis of FIG. 1 within the native mitral valve.

When displacement component 2230 approaches the underside of the native mitral valve, it may be desirable to radially collapse displacement component 2230 to cross the native mitral valve as shown in FIG. 30. If spokes 2276 of displacement component 2230 are shape set or have a mechanical memory to return to the collapsed or delivery configuration thereof, tension on pullwire 2280 is released in order to permit spokes 2276 to bend and resume their delivery configuration as shown in FIG. 30. If spokes 2276 of displacement component 2230 are shape set or have a mechanical memory to return to the expanded or deployed configuration thereof, tension on pullwire 2280 is applied in order to collapse or bend spokes 2276 into their delivery configuration as shown in FIG. 30. Once delivery sheath or capsule 529 containing collapsed heart valve prosthesis 101 is positioned within the annulus of the native mitral valve, heart valve prosthesis 101 is then deployed or expanded into apposition with the annulus of the native mitral valve as shown in FIG. 31. Alternatively, the native mitral valve may be crossed with displacement component 2230 in its expanded or deployed configuration and heart valve prosthesis 101 may be deployed with displacement component 1830 still expanded.

Figure 32:
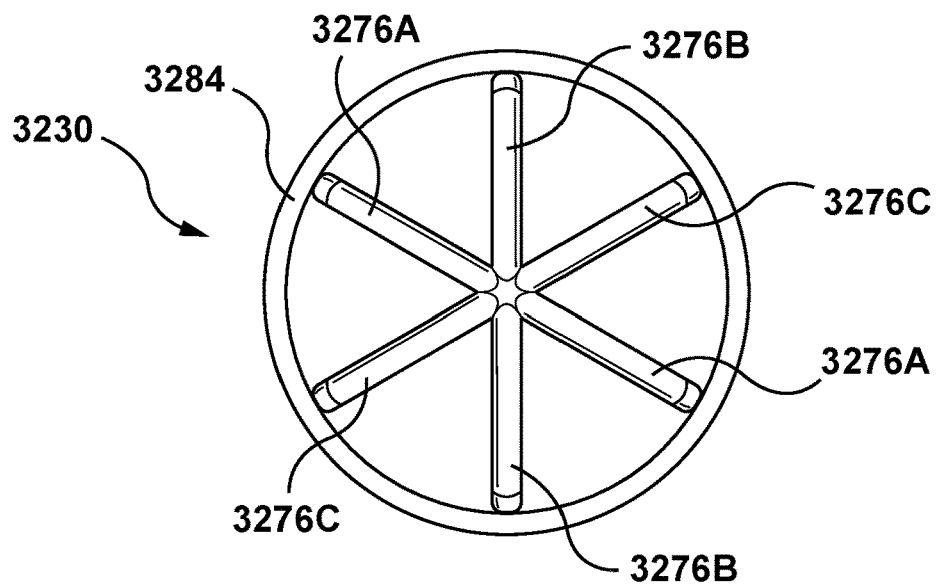
FIG. 32 is an end view of a displacement element according to another embodiment hereof, wherein the displacement component is in an expanded or deployed state and the displacement element is shown removed from the valve delivery system for illustrative purposes only.

As an alternative to planar component 2272, as depicted in FIG. 32, a displacement component 3230 may be utilized that includes a plurality of articulating arms or spokes 3276A, 3276B, 3276C (collectively referred to as spokes 3276) and an annular component 3284 that encircles and is attached to the unattached ends of spokes 3276. In this embodiment, spokes 3276A, 3276B, 3276C have the same structure and are deployed in a similar manner as spokes 2276A, 2276B, 2276C. Annular component 3284 is a ring comprised of a self-expanding material or an inflatable balloon, and functions to displace or push all chordae tendineae CT, trabeculae and ventricular bands radially outwards towards the ventricular wall and away from the valve delivery catheter during advancement of the valve delivery catheter. Spokes 3276A, 3276B, 3276C provide structural support for annular component 3284.

Further, although FIGS. 22-31 were described with utilization of pullwire 2280 to mechanically deploy spokes 2276, other deployment mechanisms may be utilized to cause spokes 2276 to radially expand as described herein. For example, hydraulic or pneumatic means may be used to deploy spokes 2276 to the expanded or deployed state.

Figure 33:
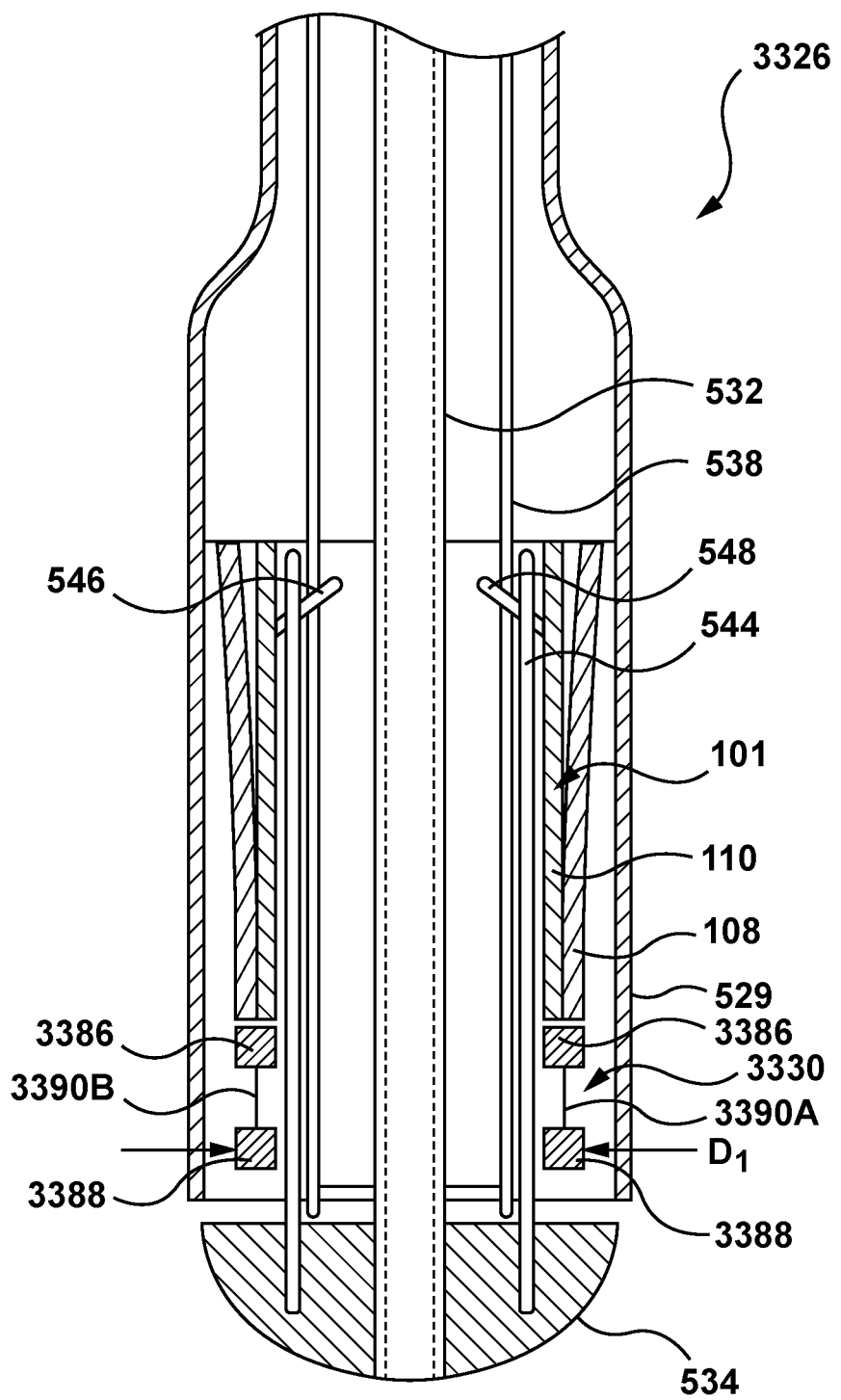
FIG. 33 is an enlarged sectional view of a distal portion of a valve delivery system according to another embodiment hereof, wherein the valve delivery system includes a displacement component including a two self-expanding rings that are longitudinally spaced apart and the displacement component is in an unexpanded or delivery state.
Figure 34:
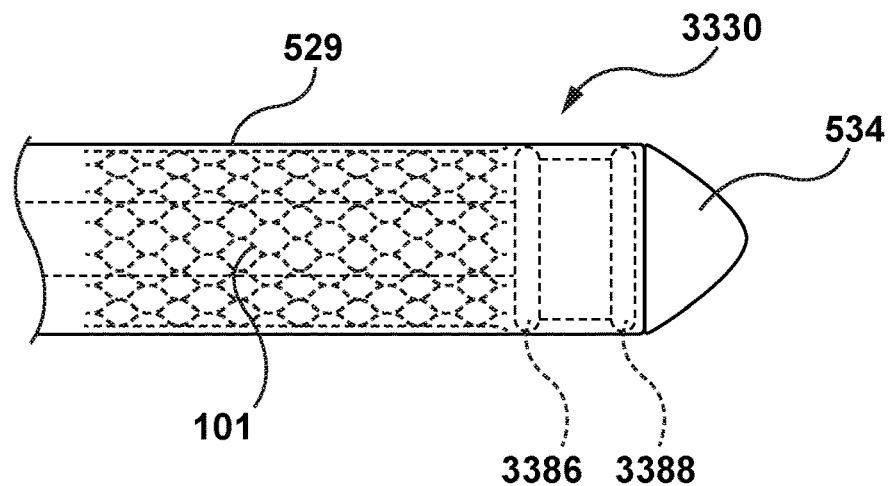
FIG. 34 is a perspective illustration of the distal portion of the valve delivery system of FIG. 33, wherein the displacement component is in the unexpanded or delivery state.

FIGS. 33-36 illustrate another embodiment of a displacement component 3330 that may be used in a valve delivery catheter 3326. FIG. 33 is an enlarged sectional view of a distal portion of valve delivery catheter 3326 with displacement component 3330 in an unexpanded or delivery state. Valve delivery catheter 3326 is similar to valve delivery catheter 526 described above except that displacement component 3330 includes a first ring 3388 comprised of a self-expanding material and a second ring 3386 comprised of a self-expanding material, first and second rings 3388, 3386 being longitudinally spaced apart and coupled to each other via a plurality of sutures or tethers 3390A, 3390B. Displacement component 3330 is incorporated onto valve delivery catheter 3326, with displacement component 3330 disposed distal to valve prosthesis 101 and compressed within a distalmost end of capsule 529 during delivery thereof as best shown in FIG. 34, and displacement component 3330 is deployed prior to valve prosthesis 101.

Figure 35:
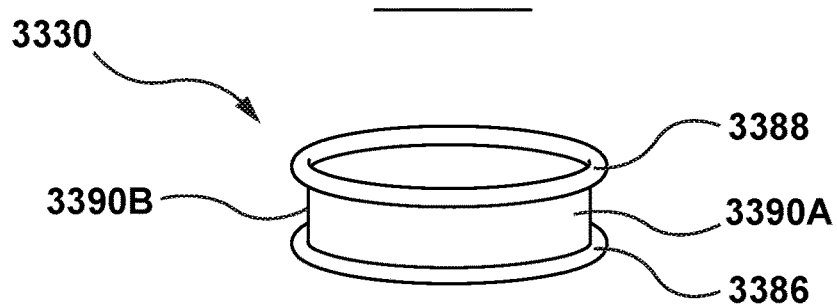
FIG. 35 is an end view of the displacement element of the valve delivery system of FIG. 33, wherein the displacement component is in an expanded or deployed state and the displacement element is shown removed from the valve delivery system for illustrative purposes only.

FIG. 35 illustrates displacement element 3330 in an expanded or deployed state and removed from the valve delivery system for illustrative purposes only. First and second rings 3388, 3386 are each annular components of an O-shape. In another embodiment hereof, one or both of first and second rings 3388, 3386 may be a C-shape. First and second rings 3388, 3386 are attached to each other via sutures or tethers 3390A, 3390B which extend between the first and second rings on opposing sides thereof. Sutures 3390A, 3390B may be formed from a monofilament or plastic suture material, such as polypropylene. First and second rings 3388, 3386 also attached to valve delivery catheter 3326 at all times via sutures or tethers 3390A, 3390B. Sutures or tethers 3390A, 3390B extend proximally to handle 542, for example, within respective or designated lumens (not shown) formed within a sidewall of inner shaft 532, which may be formed via multi-lumen extrusion as known in the art. A suitable mechanism (not shown) on handle 542 can allow the operator to retract sutures or tethers 3390A, 3390B in a proximal direction in order to retrieve displacement component 3330 after valve deployment if desired, as will be described in more detail herein.

Figure 36:
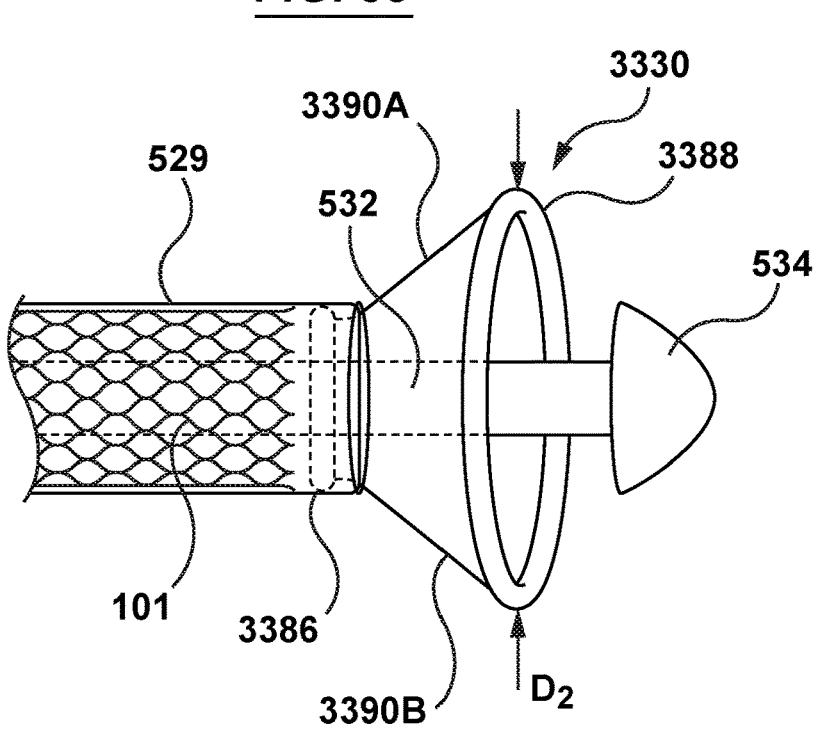
FIG. 36 is a perspective illustration of the distal portion of the valve delivery system of FIG. 33, wherein a first ring of the displacement component is in the expanded or deployed state and a second ring of the displacement component is in the unexpanded or delivery state.

FIG. 36 is a perspective illustration of the distal end of valve delivery catheter 3326 during deployment of displacement component 3330. First ring 3388 is disposed distal to second ring 3386, and thus first ring 3388 is deployed prior to second ring 3386. In FIG. 36, first ring 3388 of displacement component 3330 is in the expanded or deployed state and second ring 3386 of displacement component 3330 is in the unexpanded or delivery state. Deployment of displacement component 3330 is a two stage or step process, i.e., deployment or expansion of first ring 3388 and then deployment or expansion of second ring 3386, to allow for alignment of displacement component 3330 before completing deployment of the displacement component. Ring alignment may be adjusted through manipulation of valve delivery catheter 3326 between ring deployment procedural steps.

Displacement component 3330 may be used to displace or push all chordae tendineae CT, trabeculae and ventricular bands radially outwards towards the ventricular wall and away from the valve delivery catheter during advancement of valve delivery catheter 3326. As described with respect to FIGS. 9-13 herein, valve delivery catheter 3326 is introduced into a ventricle of the heart through a puncture in the ventricle wall at or near the apex of the heart and is sealed by a purse-string suture. Valve delivery catheter 3326 is positioned into the left ventricle via a transapical approach and positioning valve delivery catheter 3326 within the left ventricle of the heart includes introducing the catheter into the apex of the heart as well as introducing the catheter through a ventricular wall adjacent to the apex of the heart as described above. Heart valve prosthesis 101 is in the delivery or collapsed configuration within delivery the sheath or capsule 529, and displacement component 3330 is in its delivery or unexpanded state in which the displacement component has a first or unexpanded outer diameter $D_1$ and is housed or disposed within a distalmost end of capsule 529. With heart valve prosthesis 101 still in the delivery configuration, displacement component 1830 is radially expanded via retraction of capsule 529. More particularly, capsule 529 of valve delivery catheter 3326 is proximally retracted to expose first ring 3388 and permit self-expansion thereof. After alignment of first ring 3388 is verified, capsule 529 of valve delivery catheter 3326 is further proximally retracted to expose second ring 3386 and permit self-expansion thereof. First and second rings 3388, 3386 of displacement component 3300 each have a second outer diameter $D_2$ greater than the first outer diameter $D_1$. Valve delivery catheter 3326 is then maneuvered and advanced towards the annulus of the native valve of the heart with displacement component 3330 in the expanded state. With first and second rings 3388, 3386 expanded and released from capsule 529, displacement component 3330 displaces or pushes all chordae tendineae CT, trabeculae and ventricular bands radially outwards towards the ventricular wall and away from the valve delivery catheter during advancement of valve delivery catheter 3326. The second outer diameter $D_2$ of expanded displacement component 3330 is of a dimension that prevents the displacement component from passing through openings between chordae in a left ventricle. Once delivery sheath or capsule 529 containing collapsed heart valve prosthesis 101 is positioned within the annulus of the native mitral valve, heart valve prosthesis 101 is then deployed or expanded into apposition with the annulus of the native mitral valve. After deployment of heart valve prosthesis 101, displacement component 3330 is retracted or return back into capsule 529 by pulling or proximally retracting sutures or tethers 3390A, 3390B in order to retrieve displacement component 3330 after valve deployment.

While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A method of delivering a valve prosthesis to an annulus of a native valve of a heart, the native valve having chordae tendineae, the method comprising the steps of:
    introducing a valve delivery system into a ventricle of the heart via a ventricular wall of the heart, the valve delivery system having the valve prosthesis at a distal portion thereof and a displacement component at the distal portion thereof, wherein the valve prosthesis is in a delivery configuration and the displacement component is in a delivery state in which the displacement component has a first outer diameter and wherein the displacement component includes a first ring comprised of a self-expanding material and a second ring comprised of a self-expanding material, the first and second self-expanding rings being longitudinally spaced apart and coupled to each other via a plurality of sutures;
    radially expanding the displacement component of the valve delivery system into an expanded state in which the displacement component has a second outer diameter greater than the first outer diameter, wherein the valve prosthesis is in the delivery configuration;
    advancing the valve delivery system towards the annulus of the native valve of the heart with the displacement component in the expanded state, wherein the second outer diameter is of a dimension that prevents the displacement component from passing through openings between chordae in the ventricle so that the displacement component in the expanded state pushes chordae in the ventricle radially outward away from the valve delivery system; and
    deploying the valve prosthesis into apposition with the annulus of the native valve.

2. The method of claim 1, further comprising the step of:
    at least partially radially collapsing the displacement component prior to the step of deploying the valve prosthesis.

3. The method of claim 1, wherein the step of deploying the valve prosthesis into apposition with the annulus of the native valve occurs with the displacement component in the expanded state.

4. The method of claim 1, wherein the first outer diameter is not greater than an outer diameter of an outer shaft of the valve delivery system and the second outer diameter is greater than the outer diameter of the outer shaft.

5. The method of claim 1, wherein the first and second rings are one of an O-shape or a C-shape.

6. The method of claim 1, wherein the first ring is positioned distal to the second ring and the step of radially expanding the displacement component of the valve delivery system into an expanded state includes radially expanding the first ring prior to radially expanding the second ring.

7. A delivery system for delivering a valve prosthesis, the delivery system comprising:
    an inner shaft component having a distal segment over which the valve prosthesis is loaded in a compressed delivery configuration, wherein the valve prosthesis includes a frame and a prosthetic valve component disposed within the frame;
    an outer shaft component slidingly disposed over the distal segment of the inner shaft component for holding the valve prosthesis in the compressed delivery configuration; and
    a displacement component at a distal portion of the delivery system, the displacement component disposed distal to the valve prosthesis when the valve prosthesis is in the compressed delivery configuration, wherein the displacement component includes a first ring comprised of a self-expanding material and a second ring comprised of a self-expanding material, the first and second self-expanding rings being longitudinally spaced apart and coupled to each other via a plurality of sutures, and wherein the displacement component is configured to be removed from a patient via the delivery system after deployment of the valve prosthesis.

8. The delivery system of claim 7, wherein the first and second rings are one of an O-shape or a C-shape.

9. The delivery system of claim 7, wherein the plurality of sutures include two sutures which extend between the first and second rings on opposing sides thereof.

10. The delivery system of claim 7, wherein each of the first and second rings of the displacement component is configured to be radially expandable between a first outer diameter and a second outer diameter, the second outer diameter being greater than the first outer diameter, and wherein the displacement component is held in a delivery state in which the displacement component has the first outer diameter within a distalmost end of the outer shaft component.

11. A method of delivering a valve prosthesis to an annulus of a native valve of a heart, the native valve having chordae tendineae, the method comprising the steps of:
    introducing a valve delivery system into a ventricle of the heart via a ventricular wall of the heart, the valve delivery system having the valve prosthesis at a distal portion thereof and a displacement component at the distal portion thereof, the displacement component including a first ring comprised of a self-expanding material and a second ring comprised of a self-expanding material, the first and second self-expanding rings being longitudinally spaced apart and coupled to each other via a plurality of sutures, wherein the valve prosthesis is in a delivery configuration and the displacement component is in a delivery state in which the displacement component has a first outer diameter;
    radially expanding the displacement component of the valve delivery system into an expanded state in which the displacement component has a second outer diameter greater than the first outer diameter, wherein the valve prosthesis is in the delivery configuration;
    advancing the valve delivery system towards the annulus of the native valve of the heart with the displacement component in the expanded state, wherein the second outer diameter is of a dimension that prevents the displacement component from passing through openings between chordae in the ventricle so that the displacement component in the expanded state pushes chordae in the ventricle radially outward away from the valve delivery system; and deploying the valve prosthesis into apposition with the annulus of the native valve.

12. The method of claim 11, wherein the first outer diameter is not greater than an outer diameter of an outer shaft of the valve delivery system and the second outer diameter is greater than the outer diameter of the outer shaft.

13. The method of claim 11, wherein the first and second rings are one of an O-shape or a C-shape.

14. The method of claim 11, wherein the first ring is positioned distal to the second ring and the step of radially expanding the displacement component of the valve delivery system into an expanded state includes radially expanding the first ring prior to radially expanding the second ring.

15. The method of claim 14, further comprising aligning the first ring after radial expansion thereof prior to radially expanding the second ring.

16. The method of claim 11, wherein the first and second rings each have the second outer diameter after radial expansion thereof.

17. The method of claim 11, wherein the step of deploying the valve prosthesis into apposition with the annulus of the native valve occurs with the displacement component in the expanded state.

18. The method of claim 11, wherein the native valve is a mitral valve.

19. The method of claim 11, further comprising retracting the displacement component into a capsule of the valve delivery system after deployment of the valve prosthesis.

* * * * *